US009907722B2

(12) United States Patent
Aguirre-Ollinger et al.

(10) Patent No.: US 9,907,722 B2
(45) Date of Patent: Mar. 6, 2018

(54) ADMITTANCE SHAPING CONTROLLER FOR EXOSKELETON ASSISTANCE OF THE LOWER EXTREMITIES

(71) Applicant: Honda Motor Co., Ltd., Minato-ku, Tokyo (JP)

(72) Inventors: Gabriel Aguirre-Ollinger, Chatswood (AU); Umashankar Nagarajan, Sunnyvale, CA (US); Ambarish Goswami, Fremont, CA (US)

(73) Assignee: HONDA MOTOR CO., LTD., Tokyo (JP)

( * ) Notice: Subject to any disclaimer, the term of this patent is extended or adjusted under 35 U.S.C. 154(b) by 379 days.

(21) Appl. No.: 14/750,657

(22) Filed: Jun. 25, 2015

(65) Prior Publication Data

US 2016/0045385 A1 Feb. 18, 2016

Related U.S. Application Data

(60) Provisional application No. 62/037,751, filed on Aug. 15, 2014.

(51) Int. Cl.

| | |
|---|---|
| ***A61F 2/68*** | (2006.01) |
| ***A61H 3/00*** | (2006.01) |
| ***A61H 1/02*** | (2006.01) |

(52) U.S. Cl.

CPC ............. *A61H 3/00* (2013.01); *A61H 1/0244* (2013.01); *A61H 2003/007* (2013.01);

(Continued)

(58) Field of Classification Search

CPC .... A61H 1/0262; A61H 1/024; A61H 1/0244; A61H 21/00181; A61H 3/00;

(Continued)

(56) References Cited

U.S. PATENT DOCUMENTS

| | | | |
|---|---|---|---|
| 7,190,141 | B1 | 3/2007 | Ashrafiuon et al. |
| 7,628,766 | B1 | 12/2009 | Kazerooni et al. |

(Continued)

FOREIGN PATENT DOCUMENTS

| | | |
|---|---|---|
| WO | 2013067407 | 5/2013 |
| WO | 2013136351 | 9/2013 |

(Continued)

OTHER PUBLICATIONS

Aguirre-Ollinger G, Colgate J, Peshkin M, Goswami A (2007) A 1-DOF assistive exoskeleton with virtual negative damping: effects on the kinematic response of the lower limbs. In: IEEE/RSJ International Conference on Intelligent Robots and Systems IROS 2007, pp. 1938-1944.

(Continued)

*Primary Examiner* — Glenn Richman

(74) *Attorney, Agent, or Firm* — Arent Fox LLP

(57) ABSTRACT

The control method for lower-limb assistive exoskeletons assists human movement by producing a desired dynamic response on the human leg. Wearing the exoskeleton replaces the leg's natural admittance with the equivalent admittance of the coupled system formed by the leg and the exoskeleton. The control goal is to make the leg obey an admittance model defined by target values of natural frequency, resonant peak magnitude and zero-frequency response. The control achieves these objectives objective via positive feedback of the leg's angular position and angular acceleration. The method achieves simultaneous performance and robust stability through a constrained optimization that maximizes the system's gain margins while ensuring the desired location of its dominant poles.

19 Claims, 14 Drawing Sheets

(52) U.S. Cl.
CPC ................ *A61H 2201/1207* (2013.01); *A61H 2201/164* (2013.01); *A61H 2201/165* (2013.01); *A61H 2201/1628* (2013.01); *A61H 2201/1652* (2013.01); *A61H 2201/5007* (2013.01); *A61H 2201/5079* (2013.01); *A61H 2201/5084* (2013.01)

(58) Field of Classification Search
CPC .... A61H 2201/1652; A61H 2201/5079; A61H 2201/5084; A61H 2201/1207; A61H 2201/1628; A61H 2201/164; A61H 2201/165; A61H 2003/007
See application file for complete search history.

(56) References Cited

U.S. PATENT DOCUMENTS

| | | | | |
|---|---|---|---|---|
| 8,082,062 | B2 | 12/2011 | Dariush | |
| 8,147,436 | B2 * | 4/2012 | Agrawal .......... | A63B 21/00181 602/16 |
| 8,419,804 | B2 | 4/2013 | Herr et al. | |
| 8,512,415 | B2 | 8/2013 | Herr et al. | |
| 8,801,641 | B2 | 8/2014 | Kazerooni et al. | |
| 9,604,369 | B2 * | 3/2017 | Angold ................ | A61H 1/0244 |
| 9,682,005 | B2 * | 6/2017 | Herr ......................... | A61H 3/00 |
| 9,687,409 | B2 * | 6/2017 | Teng ...................... | A61H 1/024 |
| 9,707,146 | B2 * | 7/2017 | Kwon .................. | A61H 1/0262 |
| 9,750,620 | B2 * | 9/2017 | Goldfarb ................... | A61F 2/68 |
| 9,808,073 | B1 | 11/2017 | Maxwell et al. | |
| 9,808,390 | B2 | 11/2017 | Caires et al. | |
| 9,855,181 | B2 | 1/2018 | Caires et al. | |
| 9,861,501 | B2 | 1/2018 | Yoon et al. | |
| 2007/0123997 | A1 | 5/2007 | Herr et al. | |
| 2009/0292369 | A1 | 11/2009 | Kazerooni et al. | |
| 2010/0094185 | A1 | 4/2010 | Amundson et al. | |
| 2011/0066088 | A1 | 3/2011 | Little et al. | |
| 2011/0105966 | A1 | 5/2011 | Kazerooni et al. | |
| 2011/0266323 | A1 | 11/2011 | Kazerooni et al. | |
| 2012/0221119 | A1 | 8/2012 | Goldfarb et al. | |
| 2013/0023800 | A1 | 1/2013 | Bedard et al. | |
| 2013/0046218 | A1 | 2/2013 | Wiggin et al. | |
| 2013/0310979 | A1 | 11/2013 | Herr et al. | |
| 2014/0081420 | A1 | 3/2014 | Herr et al. | |
| 2014/0142475 | A1 | 5/2014 | Goldfarb et al. | |
| 2014/0163435 | A1 | 6/2014 | Yamamoto et al. | |
| 2014/0200715 | A1 | 7/2014 | Sugar et al. | |

FOREIGN PATENT DOCUMENTS

| | | |
|---|---|---|
| WO | 2013142777 | 9/2013 |
| WO | 2013188510 | 5/2014 |

OTHER PUBLICATIONS

Aguirre-Ollinger G, Colgate J, Peshkin M, Goswami A (2011) Design of an active one-degree-of-freedom lower-limb exoskeleton with inertia compensation. The International Journal of Robotics Research 30(4).
Aguirre-Ollinger G, Colgate J, Peshkin M, Goswami A (2012) Inertia compensation control of a one-degree-of-freedom exoskeleton for lower-limb assistance: Initial experiments. Neural Systems and Rehabilitation Engineering, IEEE Transactions on 20(1):68-77.
American Honda Motor Co, Inc (2009) Honda walk assist and mobility devices. http://www.corporate.honda.com/innovation/walk-assist.
Astrom KJ, Murray RM (2008) Feedback Systems: An Introduction for Scientists and Engineers. Princeton University Press, Princeton, NJ, USA.
Banala S, Agrawal SK, Fattah A, Krishnamoorthy V, Hsu WL, Scholz J, Rudolph K (2006) Gravity-balancing leg orthosis and its performance evaluation. IEEE Transactions on Robotics 22(6):1228-1239.
Banala S, Kim S, Agrawal S, Scholz J (2009) Robot assisted gait training with active leg exoskeleton (ALEX). Neural Systems and Rehabilitation Engineering, IEEE Transactions on 17(1):2-8.
Belanger P, Dobrovolny P, Helmy A, Zhang X (1998) Estimation of angular velocity and acceleration from shaftencoder measurements. The International Journal of Robotics Research 17(11):1225-1233.
Blaya J, Herr H (2004) Adaptive control of a variable-impedance ankle-foot orthosis to assist drop-foot gait. Neural Systems and Rehabilitation Engineering, IEEE Transactions on 12(1):24-31.
Colgate J, Hogan N (1988) Robust control of dynamically interacting systems. International Journal of Control 48(1):65-88.
Colgate J, Hogan N (1989) An analysis of contact instability in terms of passive physical equivalents. Proceedings of the IEEE International Conference on Robotics and Automation pp. 404-409.
Doke J, Kuo AD (2007) Energetic cost of producing cyclic muscle force, rather than work, to swing the human leg. Journal of Experimental Biology 210:2390-2398.
Dollar A, Herr H (2008) Lower extremity exoskeletons and active orthoses: Challenges and state of the art. IEEE Transactions on Robotics 24(1):144-158.
Ekso BionicsTM (2013) Ekso bionics—an exoskeleton bionicsuit or a wearable robot that helps people walk again. http://www.eksobionics.com.
Emken J, Wynne J, Harkema S, Reinkensmeyer D (2006) A robotic device for manipulating human stepping. Robotics, IEEE Transactions on 22(1):185-189.
European Commission (CORDIS) (2013) Balance Augmentation in Locomotion, through Anticipative, Natural and Cooperative control of Exoskeletons (BALANCE). http://www.cordis.europa.eu/projects/rcn/106854_en.html.
Fee J, Miller F (2004) The leg drop pendulum test performed under general anesthesia in spastic cerebral palsy. Developmental Medicine and Child Neurology 46:273-281.
Ferris D, Sawicki G, Daley M (2007) A physiologist's perspective on robotic exoskeletons for human locomotion. International Journal of Humanoid Robotics 4:507-528.
Frazzoli E, Dahleh M (2011) 6.241J Dynamic Systems and Control (MIT OpenCourseWare). http://www.ocw.mit.edu/courses.
Gordon K, Kinnaird C, Ferris D (2013) Locomotor adaptation to a soleus EMG-controlled antagonistic exoskeleton. Journal of Neurophysiology 109(7):1804-1814.
Hogan N, Buerger S (2006) Relaxing passivity for human-robot interaction. Proceedings of the 2006 IEEE/RSJ International Conference on Intelligent Robots and Systems.
Kawamoto H, Sankai Y (2005) Power assist method based on phase sequence and muscle force condition for HAL. Advanced Robotics 19(7):717-734.
Kawamoto H, Lee S, Kanbe S, Sankai Y (2003) Power assist method for HAK-3 using EMG-based feedback controller. In: Systems, Man and Cybernetics, 2003. IEEE International Conference on, vol. 2, pp. 1648-1653 vol. 2.
Kazerooni H, Racine J, Huang R Land Steger (2005) On the control of the berkeley lower extremity exoskeleton (BLEEX). In: Proceedings of the IEEE International Conference on Robotics and Automation ICRA 2005, pp. 4353-4360.
Kuo AD (2002) Energetics of actively powered locomotion using the simplest walking model. Journal of Biomechanical Engineering 124:113-120.
Lee S, Sankai Y (2003) The natural frequency-based power assist control for lower body with HAL-3. IEEE International Conference on Systems, Man and Cybernetics 2:1642-1647.
Middleton R, Braslaysky J (2000) On the relationship be-tween logarithmic sensitivity integrals and limiting optimal control problems. Decision and Control, 2000 Proceedings of the 39th IEEE Conference on 5:4990-4995 vol. 5.
Mooney L, Rouse E, Herr H (2014) Autonomous exoskeleton reduces metabolic cost of human walking during load carriage. Journal of NeuroEngineering and Rehabilitation 11(1):80.
More J, Sorensen D (1983) Computing a trust region step. SIAM Journal on Scientific and Statistical Computing 4(3):553-572.

(56) References Cited

OTHER PUBLICATIONS

Norris J, Granata KP, Mitros MR, Byrne EM, Marsh AP (2007) Effect of augmented plantarflexion power on preferred walking speed and economy in young and older adults. Gait & Posture 25:620-627.
Petric T, Gams A, Ijspeert A, Zlajpah L (2011) On-line fre-quency adaptation and movement imitation for rhythmic robotic tasks. International Journal of Robotics Research 30(14):1775-1788.
Sawicki G, Ferris D (2008) Mechanics and energetics of level walking with powered ankle exoskeletons. Journal of Experimental Biology 211:1402-1413.
Sawicki G, Ferris D (2009) Powered ankle exoskeletons re-veal the metabolic cost of plantar flexor mechanical work during walking with longer steps at constant step frequency. Journal of Experimental Biology 212:21-31.
Stein G (2003) Respect the unstable. Control Systems, IEEE 23(4):12-25.
Tafazzoli F, Lamontagne M (1996) Mechanical behaviour of hamstring muscles in low-back pain patients and control subjects. Clinical Biomechanics 11(1):16-24.
Vallery H, Duschau-Wicke A, Riener R (2009) Generalized elasticities improve patient-cooperative control of rehabilitation robots. In: IEEE International Conference on Rehabilitation Robotics ICORR, Jun. 23-26, 2009, Kyoto, Japan, pp. 535-541.
Van Asseldonk E, Ekkelenkamp R, Veneman J, Van der Helm F, Van der Kooij H (2007) Selective control of a subtask of walking in a robotic gait trainer(LOPES). Proceedings of the IEEE International Conference on Rehabilitation Robotics pp. 841-848.
Veneman J, Ekkelenkamp R, Kruidhof R, Van der Helm F, Van der Kooij H (2005) Design of a series elastic and Bowden cable-based actuation system for use as torque-actuator in exoskeleton-type training. Proceedings of the IEEE International Conference on Rehabilitation Robotics pp. 496-499.

* cited by examiner

ADMITTANCE SHAPING CONTROLLER FOR EXOSKELETON ASSISTANCE OF THE LOWER EXTREMITIES

RELATED APPLICATIONS

The present application claims the benefit of U.S. Provisional Application No. 62/037,751, filed Aug. 15, 2014, entitled "AN ADMITTANCE SHAPING CONTROLLER FOR EXOSKELETON ASSISTANCE OF THE LOWER EXTREMITIES" in the name of the same inventors, and which is incorporated herein by reference in its entirety.

TECHNICAL FIELD

The present application generally relates to controlling an exoskeleton to assist in the motion of a user and, more particularly, to a system and method for lower-limb exoskeleton control that may assist human walk by producing a desired dynamic response of the human leg, wherein a control goal is to allow the leg to obey an admittance model defined by target values of natural frequency, resonant peak magnitude and zero-frequency response, and wherein an estimation of muscle torques or motion intent may not be necessary.

BACKGROUND

Exoskeletons are wearable mechanical devices that may possess a kinematic configuration similar to that of the human body and that may have the ability to follow the movements of the user's extremities. Powered exoskeletons may be designed to produce contact forces to assist the user in performing a motor task. In recent years, a large number of lower-limb exoskeleton systems and their associated control methods have been developed, both as research tools for the study of human gait (Ferris, D., Sawicki, G., Daley, M. "A physiologist's perspective on robotic exoskeletons for human locomotion." International Journal of Humanoid Robotics (2007) 4: pp 507-52) and as rehabilitation tools for patients with stroke and/or other locomotor disorders (Dollar, A., Herr, H. "Lower extremity exoskeletons and active orthoses: Challenges and state of the art." IEEE Transactions on Robotics (2008) 24(1): pp 144-158). In a parallel development, a number of lightweight, autonomous exoskeletons have been designed with the aim of assisting impaired and/or aged users in daily-living situations (Ekso Bionics™ "Ekso bionics—an exoskeleton bionic suit or a wearable robot that helps people walk again." (2013) URL www.eksobionics.com).

A wide variety of assistive strategies and control methods for exoskeleton devices have been developed and tested with varying levels of success. For example, an assistive strategy may be based on how exoskeleton forces or torques are applied to the human body. This strategy may treat the human body as a multi-body system composed of rigid, actuated links, such as (a) Propulsion of the body's center of mass, especially during the stance phase of walking (Kazerooni, H., Racine, J., Huang, R. Land Steger "On the control of the berkeley lower extremity exoskeleton (BLEEX)." In: Proceedings of the IEEE International Conference on Robotics and Automation ICRA (2005), pp 4353-4360); (b) Propulsion of the unconstrained leg, for example during the swing phase of walking (Veneman, J., Ekkelenkamp, R., Kruidhof, R., Van der Helm, F., Van der Kooij, H. "Design of a series elastic- and Bowden cable-based actuation system for use as torque-actuator in exoskeleton-type training." Proceedings of the IEEE International Conference on Rehabilitation Robotics (2005) pp 496-499); or (c) Gravitational support of the extremities (Banala, S., Kim, S., Agrawal, S., Scholz, J. "Robot assisted gait training with active leg exoskeleton (ALEX)." Neural Systems and Rehabilitation Engineering, IEEE Transactions (2009) on 17(1) pp 2-8).

Another assistive strategy may be based on the intended effect on the dynamics or physiology of human movement. For example, (a) Reducing the muscle activation required for walking at a given speed (Kawamoto, H., Lee, S., Kanbe, S., Sankai, Y. "Power assist method for HAL-3 using EMG-based feedback controller." In: Systems, Man and Cybernetics, IEEE International Conference (2003) in, vol 2, pp 1648-1653; Gordon, K, Kinnaird, C, Ferris, D. "Locomotor adaptation to a soleus EMG-controlled antagonistic exoskeleton." Journal of Neurophysiology (2013) 109(7): pp 1804-1814); (b) Increasing the comfortable walking speed for a given level of muscle effort (Norris, J., Granata, K. P., Mitros, M. R., Byrne, E. M., Marsh, A. P. "Effect of augmented plantarflexion power on preferred walking speed and economy in young and older adults." (2007) Gait & Posture 25: pp 620-627). The aforementioned may be attained either through an increase in mean stride length (Sawicki, G., Ferris, D. "Powered ankle exoskeletons reveal the metabolic cost of plantar flexor mechanical work during walking with longer steps at constant step frequency." Journal of Experimental Biology (2009) 212: pp 21-31) or through mean stepping frequency (Lee, S., Sankai, Y. "The natural frequency-based power assist control for lower body with HAL-3." IEEE International Conference on Systems, Man and Cybernetics (2003) 2: pp 1642-1647); (c) Reducing the metabolic cost of walking (Sawicki, G., Ferris, D. "Mechanics and energetics of level walking with powered ankle exoskeletons." Journal of Experimental Biology (2008) 211: pp 1402-1413; Mooney, L., Rouse, E., Herr. H. "Autonomous exoskeleton reduces metabolic cost of human walking during load carriage." Journal of NeuroEngineering and Rehabilitation (2014) 11(1): pp 80); (d) Correcting anomalies of the gait trajectory (Banala, S., Kim, S., Agrawal, S., Scholz, J. "Robot assisted gait training with active leg exoskeleton (ALEX)". Neural Systems and Rehabilitation Engineering, IEEE Transactions (2009) on 17(1): pp 2-8; Van Asseldonk, E., Ekkelenkamp, R., Veneman, J., Van der Helm, F., Van der Kooij, H. "Selective control of a subtask of walking in a robotic gait trainer (LOPES)." Proceedings of the IEEE International Conference on Rehabilitation Robotics (2007) pp 841-848); or (e) Balance recovery and dynamic stability during walking European Commission (CORDIS). "Balance Augmentation in Locomotion, through Anticipative, Natural and Cooperative control of Exoskeletons (BALANCE)." (2013) URL cordis.europa.eu/projects/ren/106854_en.html).

Assistive strategies based on the intended effect on the dynamics or physiology of human movement, may occur on different time scales. The effects sought may range from immediate, as in the case of balance recovery and dynamic stability, to long-term, as in the case of gait anomaly correction, which normally may become apparent over the course of several training sessions.

The approaches listed above may require the estimation of one or more of the following types of variables: kinematic state of the limb and its time derivatives, muscle torques and intended motion trajectory. Accurate estimation may be a challenging task, especially in the case of the latter two.

Despite the different assistive strategies cited above, as well as their differences in time scale, the basic interaction that may occur when wearing an exoskeleton is generally the same: the exoskeleton attempts to exert controlled forces or torques on the body segments of the user. One may define the assistive torque as the torque that should be exerted at the exoskeleton's points of contact with the user in order to help the user complete a desired motion. Designing a system and method to track a desired assistive torque may be difficult. Even assuming that reasonable estimates of the system's parameters and states may be obtained, in general, it may not be possible for an exoskeleton to deliver a completely arbitrary assistive torque profile. To do so may require the exoskeleton to behave as a pure torque source. In other words, the exoskeleton may have to display zero mechanical impedance at its port(s) of interaction with the user. Mechanical impedance may be a measure of how much the exoskeleton resists motion when subjected to a harmonic force. The mechanical impedance of a point on the exoskeleton may be defined as a ratio of the force applied at a point to the resulting velocity at that point. However, in practice, most exoskeleton mechanisms display finite mechanical impedance, thereby acting as a load on the user's limbs. In the absence of control, the coupled system formed by the leg and the exoskeleton may be less mobile than the unassisted leg. For this reason, many assistive devices feature a layer of feedback control that may be designed to reduce the exoskeleton's impedance, especially the friction effects on the user (Veneman, J., Ekkelenkamp, R., Kruidhof, R., Van der Helm, F., Van der Kooij, H. "Design of a series elastic- and Bowden cable-based actuation system for use as torque-actuator in exoskeleton-type training." Proceedings of the IEEE International Conference on Rehabilitation Robotics (2005) pp 496-499). However, the feedback control may be used not only to reduce the exoskeleton's impedance but, with proper hardware and control design, to turn the exoskeleton's port impedance into a source of assistance to the user. It would thus be desirable to provide a system and method to produce this form of impedance-based assistance. The system and method may assist by producing a desired dynamic response of the human leg, wherein the exoskeleton control may allow the leg of the user to obey an admittance model defined by target values of natural frequency, resonant peak magnitude and zero-frequency response.

SUMMARY

In accordance with one embodiment, an exoskeleton system for assisted movement of legs of a user is disclosed. The exoskeleton system has a harness worn around a waist of the user. A pair of arm members is coupled to the harness and to the legs. The exoskeleton system has a pair of motor devices. One of the pair of motor devices is coupled to a corresponding arm member of the pair of arm members moving the pair of arm members for assisted movement of the legs. A controller is coupled to the motor controlling movement of the assisted legs. The controller shapes an admittance of the system facilitating movement of the assisted legs by generating a target DC gain, a target natural frequency and a target resonant peak.

In accordance with one embodiment, a device for controlling an exoskeleton system is disclosed. The device has a controller shaping an admittance of the system facilitating movement of assisted legs coupled to the system. The controller models dynamics of one of the legs as a transfer function of a linear time-invariant (LTI) system. The controller replaces admittance of the one of the legs by an approximate equivalent admittance of a coupled leg and system by generating a target DC gain, a target natural frequency and a target resonant peak.

In accordance with one embodiment, a method for an exoskeleton assistive control is disclosed. The method comprises: calculating ratios between unassisted leg movement and a desired value through natural frequencies, resonant peaks and DC gains of the exoskeleton; calculating angular position feedback gain $k_{DC}$ of the exoskeleton system; calculating target admittance parameters $\omega^{d}_{nh}$ and $\zeta^{d}_{h}$; obtaining a dominant pole of a target admittance as $p_h^d=\sigma_h^d+j\omega_{dh}^d$; obtaining parameters $\{\sigma_f, \omega_{d,f}\}$ of a feedback compensator of the exoskeleton system; and obtaining a loop gain $K_L$ and an inertia compensation gain $I_c$ of the coupled exoskeleton system and legs of a user.

BRIEF DESCRIPTION OF DRAWINGS

In the descriptions that follow, like parts are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein.

DESCRIPTION OF THE APPLICATION

Figure 1B:
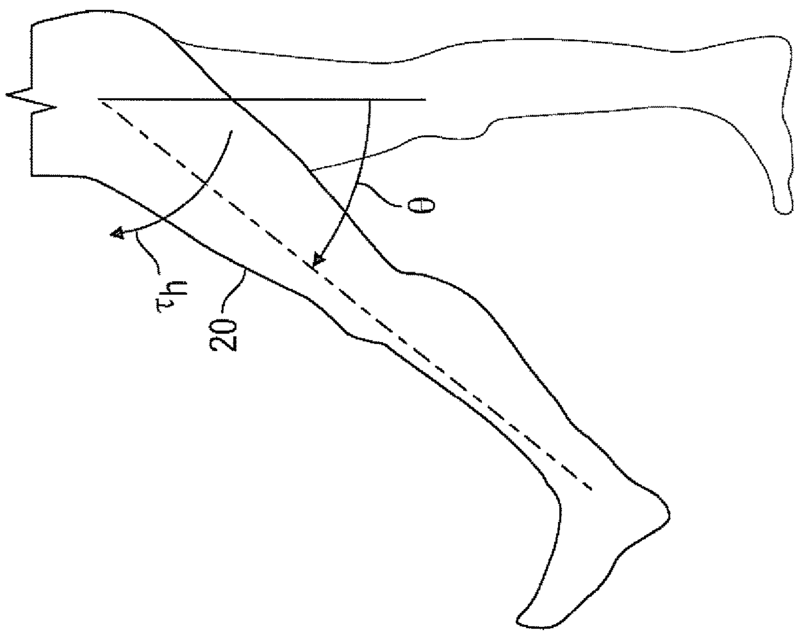
FIG. 1B is a side view of an illustrative leg swinging about a hip joint on a sagittal plane in accordance with one aspect of the present application.

The description set forth below in connection with the appended drawings is intended as a description of presently preferred embodiments of the disclosure and is not intended to represent the only forms in which the present disclosure may be constructed and/or utilized. The description sets forth the functions and the sequence of steps for constructing and operating the disclosure in connection with the illustrated embodiments. It is to be understood, however, that the same or equivalent functions and sequences may be accomplished by different embodiments that are also intended to be encompassed within the spirit and scope of this disclosure.

The present approach to exoskeleton control may define assistance in terms of a desired dynamic response for the leg, specifically a desired mechanical admittance. Leg dynamics may be modeled as the transfer function of a linear time-invariant (LTI) system. Its admittance may be a single- or multiple-port transfer function relating the net muscle torque acting on each joint to the resulting angular velocities of the joints. When the exoskeleton is coupled to the leg, the admittance of the human leg may get replaced, in a sense, by the admittance of the coupled leg-exoskeleton system (hereinafter referred to simply as "the coupled system").

The present system and method may make this admittance modification work to the user's advantage. The resulting admittance of the assisted leg may facilitate the motion of the lower extremities, for example, by reducing the muscle torque needed to accomplish a certain movement, or by enabling quicker point-to-point movements than what the user may accomplish without assistance. The advantage of this approach is that it generally does not rely on predicting the user's intended motion or attempt to track a prescribed motion trajectory.

The control system and method of the application, which one may refer to as admittance shaping, may be formulated by linear control. The design objective may be to make the equivalent admittance of the assisted leg (which is the same as the admittance of the coupled system) meet certain specifications of frequency response. Once this desired admittance has been defined, the control system and method may consist of generating a port impedance on the exoskeleton, through a state feedback function, such that when the exoskeleton is attached to the human limb, the coupled system may exhibit the desired admittance characteristics. Thus the above issue may be classified as one of interaction controller design (Buerger, S., Hogan, N. "Complementary stability and loop shaping for improved human-robot interaction." Robotics, IEEE Transactions (2007) on 23(2): pp 232-244).

The system and method provides a formulation of admittance shaping control for single-joint motion that may employ linearized models of the exoskeleton and the human limb. The system and method may be a generalization of exoskeleton controls developed around the idea of making the exoskeleton's admittance active. The system and method may involved emulated inertia compensation (Aguirre-Ollinger, G., Colgate, J., Peshkin, M., Goswami, A. "Design of an active one-degree-of-freedom lower-limb exoskeleton with inertia compensation." The International Journal of Robotics Research (2011) 30(4); Aguirre-Ollinger, G., Colgate, J., Peshkin, M., Goswami, A. "Inertia compensation control of a one-degree-of-freedom exoskeleton for lower-limb assistance: Initial experiments." Neural Systems and Rehabilitation Engineering, IEEE Transactions (2012) on 20(1): pp 68-77) or negative damping (Aguirre-Ollinger, G., Colgate, J., Peshkin, M., Goswami, A. "A 1-DOF assistive exoskeleton with virtual negative damping: effects on the kinematic response of the lower limbs" In: IEEE/RSJ International Conference on Intelligent Robots and Systems IROS (2007), pp 1938-1944). Although the notion of modifying the dynamics of the human limb may somehow be implicit in methods like the "subject comfort" control of the HAL exoskeleton (Kawamoto, H., Sankai, Y. "Power assist method based on phase sequence and muscle force condition for HAL." Advanced Robotics (2005) 19(7): pp 717-734) and the generalized elasticities control proposed by Vallery (Vallery, H., Duschau-Wicke, A., Riener, R. "Generalized elasticities improve patient-cooperative control of rehabilitation robots." In: IEEE International Conference on Rehabilitation Robotics ICORR (2009), June 23-26, Kyoto, Japan, pp 535-541), in those methods the exoskeleton's port impedance remains passive, and as such does not assist the human limb. Thus, an additional layer of active control may be needed in those methods.

The present system and method may render the exoskeleton port impedance active by means of positive feedback of the exoskeleton's kinematic state. This approach may have some similarity with the control of the BLEEX exoskeleton (Kazerooni, H., Racine, J., Huang, R. Land Steger. "On the control of the berkeley lower extremity exoskeleton (BLEEX)." In: Proceedings of the IEEE International Conference on Robotics and Automation ICRA (2005), pp 4353-4360), in which positive feedback may make the device highly responsive to the user's movements. However, in that system the actual assistance comes in the form of gravitational support of an external load. By contrast, in the present system and method, the interaction controller makes a positive feedback a source of the assistive effect.

The design of the present interaction controller may solve the following problems concurrently: performance, i.e. producing the desired admittance, and the stabilization of the coupled system. As explained below, for the exoskeleton's assistive control, the dynamic response objectives embodied by the desired admittance, may tend to trade off against the stability margins of the coupled system. At the same time, the coupled system may involve a considerable level of parameter uncertainty, especially when it comes to the dynamic parameters of the leg and the parameters of the coupling between the leg and the exoskeleton. Therefore the design may need to ensure a sufficient level of robustness for the controller's performance and stability.

The below analysis covers the following aspects: (a) Formulation of the assistive effect in terms of a target admittance (and the integral thereof) for the assisted leg. (b) Design of the exoskeleton's assistive control, more specifically, the design of the assistive control using positive feedback and how to ensure the stability of the coupled system. (c) Robust stability analysis of the assistive control.

Below, three basic forms of assistance are modeled as perturbations of the human leg's dynamic parameters, namely inertia, damping and stiffness. Next, a general-purpose definition of exoskeleton assistance formulated in terms of the limb's sensitivity transfer function is given. This transfer function may provide a measure of how the dynamic response of the leg may be affected by the above perturbations. The definition may be formulated using the Bode sensitivity integral theorem (Middleton, R., Braslaysky, J. "On the relationship between logarithmic sensitivity integrals and limiting optimal control problems." Decision and Control, (2000) Proceedings of the 39th IEEE Conference on 5:4990-4995 vol. 5). As may be shown, the Bode sensitivity integral theorem may provide a general avenue for the design of the assistive control, namely the use of positive feedback of the exoskeleton's kinematic state.

In order to develop the present mathematical formulation for lower-limb assistance, one may use a specific exoskeleton system as an example. The Stride Management Assist (SMA) device 10, shown in FIG. 1A, is an autonomous powered exoskeleton device developed by Honda Motor Co., Ltd. (Japan). The SMA device 10 may feature a harness 12. The harness 12 may be worn around a waist of a user 14 of the device 10. The harness 12 may have a housing 16. The housing 16 may store two flat brushless motors 18. Each of the motors 18 may be positioned concentric with the axis of each hip joint on the sagittal plane. The motors 18 may exert torque on the user's legs 20 through a pair of arms 22 coupled to the thighs. The arms 22 may be formed of a rigid and lightweight material. This configuration may make the SMA device 10 effective in assisting the swing phase of the walking cycle as well as other leg movements not involving ground contact.

A controller 24 may be positioned within the housing 16. The controller 24 may be used to control operation of the device 10. The controller 24 may have an angle feedback compensator 24A and an angular acceleration feedback compensator 24B as described below. A "controller," as used herein, processes signals and performs general computing and arithmetic functions. Signals processed by the controller 24 may include digital signals, data signals, computer instructions, processor instructions, messages, a bit, a bit stream, or other means that can be received, transmitted and/or detected. Generally, the controller 24 may be a variety of various microcontroller and/or processors including multiple single and multicore processors and co-processors and other multiple single and multicore processor and co-processor architectures. The processor can include various modules to execute various functions.

The controller 24 may store a computer program or other programming instructions associated with a memory 26 to control the operation of the device 10 and to analyze the data received. The data structures and code within the software in which the present application may be implemented, may typically be stored on a non-transitory computer-readable storage. The storage may be any device or medium that may store code and/or data for use by a computer system. The non-transitory computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing code and/or data now known or later developed. The controller 24 may comprise various computing elements, such as integrated circuits, microcontrollers, microprocessors, programmable logic devices, etc., alone or in combination to perform the operations described herein.

Figure 1A:
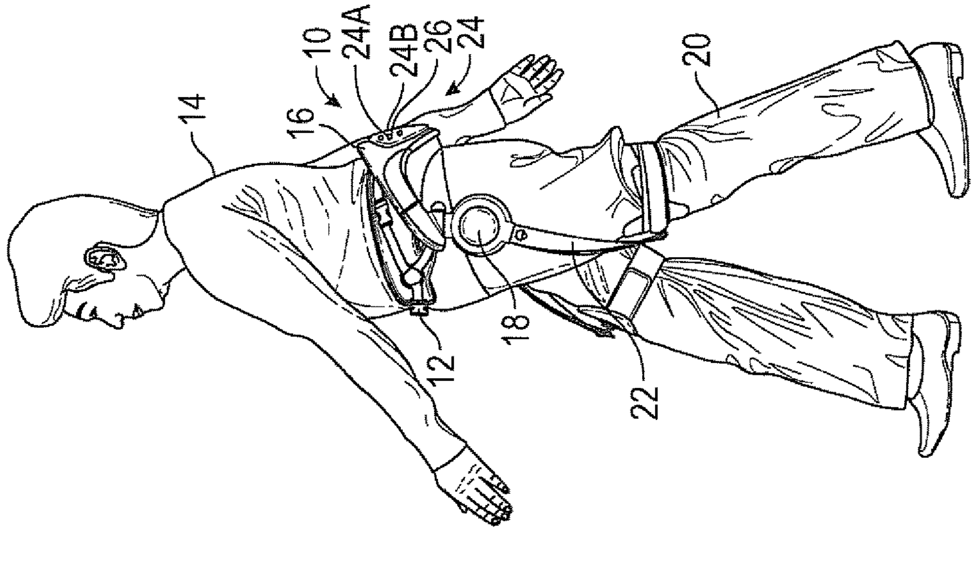
FIG. 1A is a perspective view of an exoskeleton device implementing an exemplary admittance shaping controller in accordance with one aspect of the present application.

Referring to FIG. 1B, in the human gait cycle, the swing phase may take advantage of the pendulum dynamics of the leg 20 (Kuo, A. D. "Energetics of actively powered locomotion using the simplest walking model." Journal of Biomechanical Engineering (2002) 124:113-120). The pendulum dynamics of the leg refer to the leg 20 behaving like a pendulum, possibly allowing for an energy-economical gait. An advantage of a pendulum is that it may conserve mechanical energy and thus requires little or no mechanical work to produce motion at the pendulum's natural frequency. Therefore, for the present analysis, one may model the leg 20 as a linear rotational pendulum. As may be seen in FIG. 1B, the present model may be an approximate representation of the extended leg 20 swinging about the hip joint on the sagittal plane. As humans move, they may change the stiffness of their joints in order to interact with their surroundings. Joint stiffness is the ratio of the net torque acting on the joint to the angular displacement of the joint. The impedance of the leg 20 at the hip joint, $Z_h(s)$, is the transfer function relating the net muscle torque acting on that joint, $\tau_h(s)$, to the resulting angular velocity of the leg $\Omega_h(s)$:

$$Z_h(s) = \frac{\tau_h(s)}{\Omega_h(s)} = I_h s + b_h + \frac{k_h}{s} \tag{1}$$

where $I_h$ is the moment of inertia of the leg 20 about the hip joint, and $b_h$ and $k_h$ are, respectively, the damping and stiffness coefficients of the joint. The coefficient $k_h$ may include both the stiffness of the joint's structure and a linearization of the action of gravity on the leg 20.

In order to make the treatment general, all transfer functions in this analysis may be expressed in terms of dimensionless variables. Under this assumption, a unity moment of inertia may be equal to the moment of inertia of the leg 20 about the hip joint; a unity angular frequency may equal the natural undamped frequency of the leg 20. Based on published data (Tafazzoli, F., Lamontagne, M. "Mechanical behaviour of hamstring muscles in low-back pain patients and control subjects." Clinical Biomechanics (1996) 11(1): 16-24), one may set the damping ratio of the hip joint to $\zeta_h$=0.2, which yields the following values for the coefficients in (1): $I_h$=1, $b_h$=0.4 and $k_h$=1.

One may model the effect of assisting the human limb as applying an additive perturbation $\delta Z_h$ to the limb's natural impedance $Z_h$. Here a perturbation is defined as a deviation from the normal impedance value, caused by an outside influence. The perturbed impedance is defined as:

$$\tilde{Z}_h = Z_h + \delta Z_h \quad (2)$$

An equivalent expression may be given in terms of the leg's admittance, $Y_h(s)\ Z_h(s)^{-1}$. The perturbed admittance, $\tilde{Y}(s)$, may be represented as a negative feedback system formed by $Y_h$ and $\delta Z_h$:

$$\tilde{Y}_h = \frac{1}{Z_h + \delta Z_h} = \frac{Y_h}{1 + Y_h \delta Z_h} \quad (3)$$

The task now is to determine what may make $\delta Z_h$ a properly assistive perturbation. In other words, what kind of perturbation may make $\tilde{Y}_h$ an improvement over the leg's normal admittance $Y_h$. Noting that each term on the right-hand side of (1) contributes to the overall impedance of the leg 20, the analysis may start by studying the effects of compensating each of the leg's dynamic properties, i.e. reducing its effective damping, inertia, or stiffness. Accordingly one may define the following types of perturbation.

$$\delta Z_h = \delta b_h \text{(damping perturbation)}$$

$$\delta Z_h = \delta I_h s \text{ (inertia perturbation)}$$

$$\delta Z_h = \delta k_h / s \text{ (stiffness perturbation)} \quad (4)$$

Compensation means that some or all of the terms $\delta b_h$, $\delta I_h$ or $\delta k_h$ may have negative values. One may analyze the individual effects of those perturbations on the frequency response of the integral admittance $\hat{Y}(s)/s$, which relates the net muscle torque to the angular position of the leg 20. One may use this instead of the admittance in order to include the effects on the "DC gain" (zero-frequency response) of the leg's response as well. It should be noted that at this point one is generally not concerned with the physical realization of these perturbations but their theoretical effects.

Figure 2A:
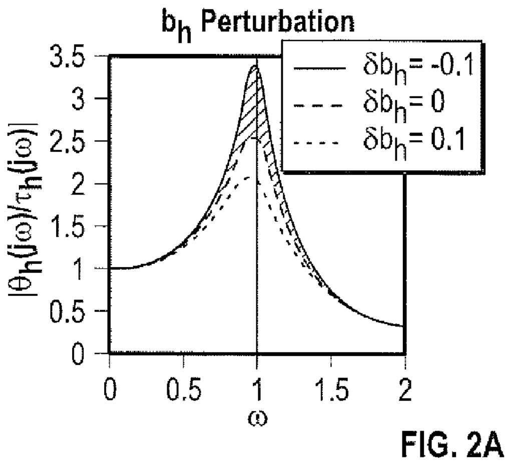
FIGS. 2A-2F are illustrative graphs showing the effects of impedance perturbations on the frequency response of an integral admittance of a human leg in accordance with one aspect of the present application.
Figure 2D:
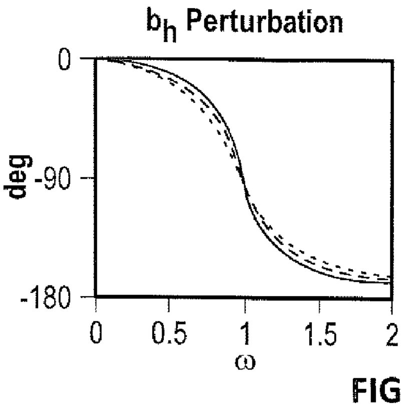
Figure 2B:
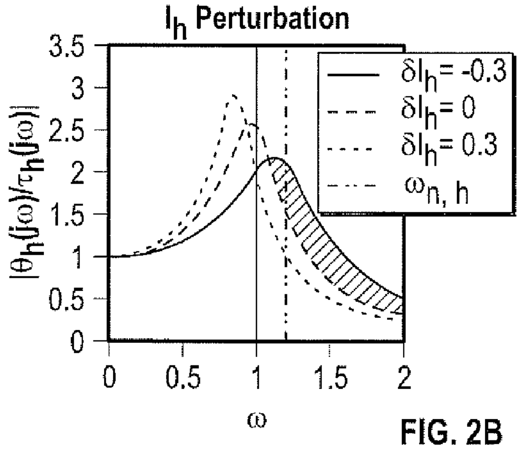
Figure 2E:
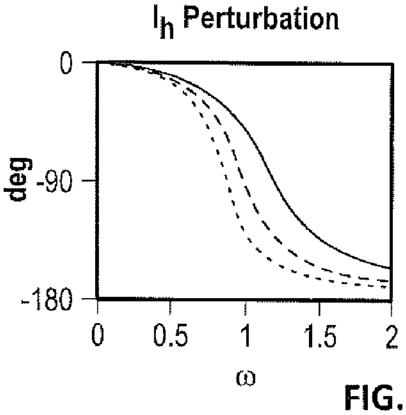
Figure 2C:
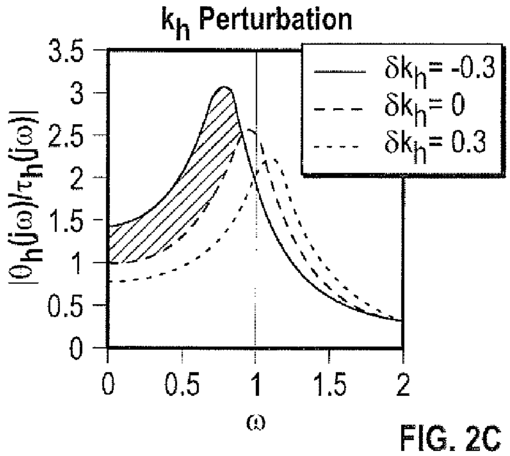
Figure 2F:
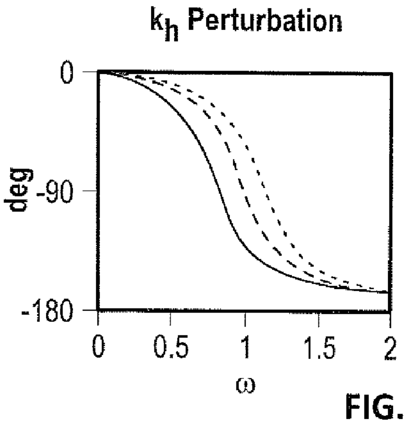

Referring to FIGS. 2A-2F, the effects of each perturbation applied individually on the integral admittance may be seen. In FIGS. 2A-2F, the effects of the impedance perturbations on the frequency response (magnitude ratio and phase) of the integral admittance of the human leg for damping perturbations (FIG. 2A and FIG. 2D); inertia perturbations (FIG. 2B and FIG. 2E); and stiffness perturbations (FIG. 2C and FIG. 2F) may be seen. The effects of both negative and positive perturbations may be seen. The gray areas in FIGS. 2A-2C may highlight portions where a negative perturbation may cause a reduction in magnitude ratio. For a given angle amplitude, these gray areas may represent "effort reduction", i.e. a reduction in the required muscle torque amplitude with respect to the unperturbed admittance. Although the main interest may be compensation, i.e. applying negative values of $\delta b_h$, $\delta I_h$ and/or $\delta k_h$, one may plot the effects of the positive ones as well for comparison. Examination of FIGS. 2A-2F reveals several aspects of the perturbed frequency responses that may be considered assistive. In FIG. 2A and FIG. 2D, damping compensation may increase the peak magnitude of the integral admittance. Thus, for given angular trajectories near the natural frequency ($\omega=1$), the amplitude of the required muscle torque may be reduced with respect to the unperturbed case. One may refer to this effect as "effort reduction". In FIG. 2B and FIG. 2E, inertia compensation may cause an increase in the natural frequency of the leg with no change in the DC gain. Thus, given a desired amplitude of angular motion, the minimum muscle torque amplitude may now occur at a higher frequency. One may hypothesize that a shift in natural frequency may have a potential beneficial effect on the gait cycle. The gait cycle is the time period or sequence of events or movements when one foot contacts the ground to when that same foot again contacts the ground. Thus, a shift in natural frequency may enable the user to walk at higher stepping frequencies without a significant increment in muscle activation (Doke, J., Kuo, A. D. "Energetic cost of producing cyclic muscle force, rather than work, to swing the human leg." Journal of Experimental Biology (2007) 210:2390-2398). A higher natural frequency may also imply a quicker transient response, which may enable the user to take quicker reactive steps when trying to avoid a fall. In FIG. 2C and FIG. 2F, stiffness compensation may produce an effort reduction at frequencies below the natural frequency.

The above observations focus on the possible benefits of the applied compensations. However, each case may have drawbacks as well. For example, the effect of damping compensation may vanish as the motion frequency departs from the natural frequency value. Inertia compensation may cause an effort increase at frequencies immediately below the natural frequency. Stiffness compensation may reduce the natural frequency of the leg, which may adversely affect the dynamics of the gait cycle.

However, these negative aspects may simply mean that no single perturbation should constitute the totality of the assistive action. By applying the principle of superposition, it may be possible to devise a perturbation transfer function that combines the beneficial aspects of each individual type of perturbation. In this way, the resulting admittance may simultaneously produce increases in the natural frequency, magnitude peak and DC gain of the leg with respect to the unassisted case.

As for perturbations involving positive values of $\delta b_h$, $\delta I_h$ and/or $\delta k_h$, one may refer to these as being resistive to indicate they have the opposite effect. Without claiming this to be an absolute statement, one may view these types of perturbations as having the tendency to reduce the leg's mobility. For example, a positive $\delta b_h$, may increases the damping of the leg, which in turn may increase the muscle effort required to produce a desired motion as may be seen in FIG. 2B. Increasing the stiffness of the leg with a positive $\delta k_h$ (for example by using a torsional spring) might be a simple way of increasing the natural frequency, but it may come at the cost of requiring increased effort at low frequencies as may be seen in FIG. 2C.

One thing that needs to be considered is how to design an exoskeleton controller capable of generating an equivalent leg admittance with arbitrary properties of natural frequency, magnitude peak and DC gain. One approach may be to make the exoskeleton emulate the negative variations of $\delta b_h$, $\delta I_h$ and/or $\delta k_h$ described above. It should be noted that such analysis does not attempt to determine what is the best admittance for the user's needs but rather to enable the exoskeleton to physically generate a desired admittance regardless of the criteria that were used to specify it.

One may derive a general principle for the design of exoskeleton control, namely the need for the exoskeleton to display active behavior. In other words, to turn the exoskeleton into a source of energy to move the legs. To this end one may introduce the notion of perturbation sensitivity (i.e., how sensitive is the exoskeleton to the different perturbations). From (3), the sensitivity transfer function $S_h(s)$ of the perturbed leg is:

$$S_h(s) = \frac{1}{1 + Y_h(s)\delta Z_h(s)} = \frac{1 + \frac{1}{I_h}\left(\frac{b_h}{s} + \frac{k_h}{s^2}\right)}{1 + \frac{1}{I_h}\left(\frac{b_h}{s} + \frac{k_h}{s^2} + \frac{\delta Z_h}{s}\right)} \quad (5)$$

This transfer function provides a measure of how the system's input/output relationship may be influenced by perturbations to its dynamic parameters. In the absence of perturbations, $S_h$ evaluates to 1 for all frequencies. Thus, $S_h(j\omega)$ may be seen as a weighting function that describes how the applied perturbation may change the shape of the leg's frequency response. The perturbed admittance is:

$$\tilde{Y}_h = S_h Y_h \quad (6)$$

One may restrict the present analysis to perturbations of which the effect vanishes at high frequencies, i.e. $|S_h| \to 1$ as $\omega \to \infty$. From equation (5) we see that this is the case for all but the inertia perturbation (4). However, the vanishing condition may easily be enforced by redefining the inertia perturbation as:

$$\delta Z_h = \delta I_h \frac{\omega_o s}{s + \omega_o} \quad (7)$$

Choosing $\omega_o >> 1$ (i.e. making it larger than the natural frequency of the leg) may ensure that the perturbation maintains its desired behavior in the general frequency range of leg motion.

A property of sensitivity transfer functions known as the Bode sensitivity integral, may allow one to derive a general principle for the design of exoskeleton control. The Bode sensitivity integral theorem (Middleton, R., Braslaysky, J. "On the relationship between logarithmic sensitivity integrals and limiting optimal control problems." Decision and Control, (2000) Proceedings of the 39th IEEE Conference on 5:4990-4995 vol. 5) is stated as follows:

Let L(s) be a proper, rational transfer function of relative degree $N_r$. The relative degree of a transfer function is be the difference between the order of the denominator and the order of the numerator. D e fi n e the closed-loop sensitivity function $S(s)=(1+L(s))^{-1}$ and assume that neither L(s) nor S(s) have poles or zeros in the closed right half plane. Then, $$\int_0^\infty \ln|S(j\omega)|\, d\omega = \begin{cases} 0 & \text{if } N_r > 1 \\ -\frac{\pi}{2}\lim_{s\to\infty} sL(s) & \text{if } N_r = 1 \end{cases} \quad (8)$$

One may use the theorem to analyze the leg's sensitivity to perturbations by defining the loop transfer function $L_h(s) = Y_{11}(s)\delta Z_h(s)$. Evaluating the Bode sensitivity integral for the perturbations previously defined yields:

$$\int_0^\infty \ln|S_h(j\omega)|\, d\omega = \quad (9)$$

$$-\frac{\pi}{2}\lim_{s\to\infty} sY_h(s)\delta Z_h(s) = \begin{cases} -\frac{\pi\delta b_h}{2I_h} & \text{for } \delta Z_h = \delta b_h \\ -\frac{\pi\delta I_h\omega_o}{2I_h} & \text{for } \delta Z_h = \delta I_h\frac{\omega_o s}{s+\omega_o} \\ 0 & \text{for } \delta Z_h = \frac{\delta k_h}{s} \end{cases}$$

Figure 3A:
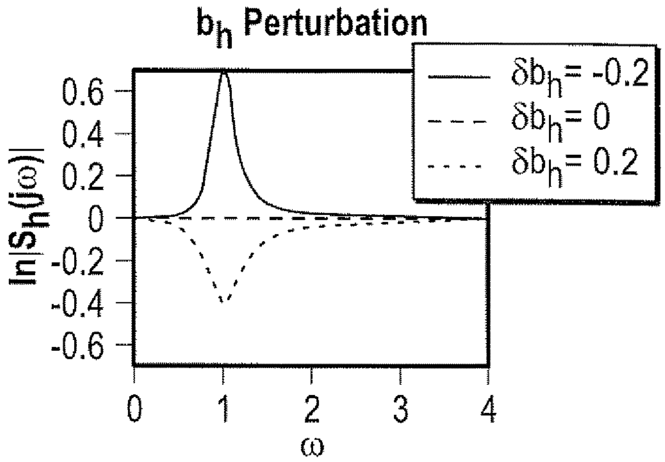
FIG. 3A-3C are exemplary sensitivity plots for impedance perturbations in accordance with one aspect of the present application.
Figure 3B:
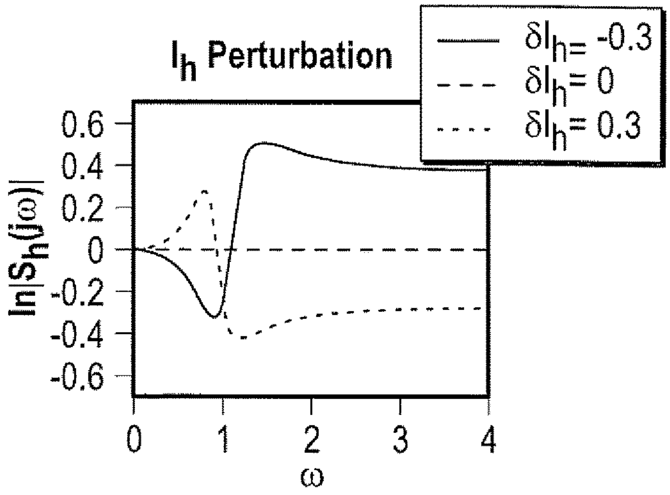
Figure 3C:
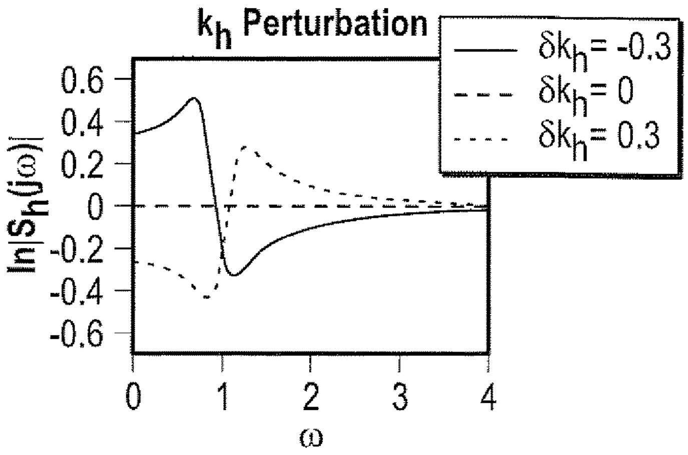

In this way one arrives at a compact result: with the exception of stiffness, negative-valued perturbations cause the area under $\ln|S_h(j\omega)|$ to be positive and vice versa. In other words, assistive perturbations with the exception of stiffness cause a net increase in sensitivity, whereas resistive perturbations cause a net decrease. For stiffness perturbations, the area under $\ln|S_h(j\omega)|$ remains constant. This means that, if the sensitivity increases in one frequency range, it will be attenuated in the same proportion elsewhere. To illustrate these points, FIG. 3A-3C shows plots of $\ln|S_h(j\omega)|$ vs. ω for different types of perturbation. As may be seen, FIG. 3A shows plots of $\ln|S_h(j\omega)|$ vs. ω for damping perturbation; FIG. 3B shows plots of $\ln|S_h(j\omega)|$ vs. ω for inertia perturbation; and FIG. 3C shows plots of $\ln|S_h(j\omega)|$ vs. ω for stiffness perturbation.

In (3) the perturbed admittance is represented as the coupling of two dynamic systems: the leg's original admittance $Y_h$, and the impedance perturbation $\delta Z_h$. Given that one may want to design a controller for the coupled system formed by the leg and the exoskeleton, (3) may suggest a simple design strategy: substitute $\delta Z_h$ with the exoskeleton's impedance, $Z_e(s)$, and design a control to make $Z_e(s)$ emulate the behavior of $S_h(s)$ as closely as possible.

The sensitivity transfer function of the coupled system formed by the leg and the exoskeleton is defined as:

$$S_{he}(s) = \frac{1}{1 + Y_h(s)Z_e(s)} \quad (10)$$

and its loop transfer function as $L_{he}(s)=Y_h(s)Z_e(s)$. One may now consider the results from the preceding section.

For the coupled system to emulate assistive (i.e. negative) perturbations of inertia or damping, the Bode sensitivity integral of $S_{he}(s)$ should be positive. From (8), it may be seen that one way to accomplish this may be by making the gain of $Z_e(s)$ negative. In other words, the exoskeleton may have to form a positive feedback loop with the human leg. An effect of the gain being negative is that the exoskeleton will display active behavior. In other words, the exoskeleton may act as an energy source. This can be deduced from the definition of a passive system transfer function: a 1-port transfer function Z (s) is said to be passive (Colgate, J., Hogan, N. "An analysis of contact instability in terms of passive physical equivalents." Proceedings of the IEEE International Conference on Robotics and Automation (1989) pp 404-409) if: (a) Z(s) has no poles in the right-hand half of the complex plane; and (b) Z(s) has a NyQuist plot that lies wholly in the right-hand half of the complex plane.

It follows from the second condition that the phase of Z(jω) should lay within −90° and 90° for all ω. With the exoskeleton transfer function $Z_e(s)$ this is not the case because the negative gain introduces a phase shift of −180° at all frequencies. Therefore $Z_e(s)$ is active. Active behavior may be consistent with the exoskeleton's role as an assistive device since it may enable the exoskeleton to perform net positive work on the leg over one gait cycle. By contrast, a passive exoskeleton is limited to dissipating energy from the human limb, or at best to altering the balance between the kinetic and potential energies of the leg.

On the other hand, active behavior may raise the issue of coupled stability. Colgate, J., Hogan, N. (1988) "Robust control of dynamically interacting systems." International Journal of Control (1988) 48(1):65-88 has shown that a manipulator remains stable when coupled to an arbitrary passive environment if the manipulator itself is passive. As a result, ensuring manipulator passivity has become an accepted criterion for ensuring stable human-robot interaction (Hogan, N., Buerger, S. "Relaxing passivity for human-robot interaction." Proceedings of the 2006 IEEE/RSJ International Conference on Intelligent Robots and Systems (2006)). However, passive behavior may limit performance. In the case of an exoskeleton, passive behavior may render the exoskeleton incapable of providing assistance, at least per the criteria outlined above. But then, the requirement may not be to ensure stable interaction with every possible passive environment, but with a certain class of environments, namely those possessing the typical dynamic properties of the human leg.

Limiting the set of passive environments with which the exoskeleton is intended to interact may allow one to use a less restrictive stability criterion. For example, stability may be guaranteed by the Bode criterion for positive feedback:

$$|-Y_h(j\omega)Z_e(j\omega)<1$$

$$\text{where } \angle(-Y_h(j\omega)Z_e(j\omega))=160° \tag{11}$$

Below, the formulation of a stable assistive controller capable of generating an equivalent leg admittance with arbitrary values of natural frequency, resonant peak and, for the integral admittance, DC gain, is presented.

The present control design specifications are based on the human limb's integral admittance, $X_h(s)=Y_h(s)/s$, expressed in terms of dynamic response parameters:

$$X_h(s) = \frac{1}{I_h(s^2 + 2\zeta_h\omega_{nh}s + \omega_{nh}^2)} \tag{12}$$

Where $\omega_{nh}$ is the natural frequency of the leg and $\zeta_h$ is the damping ratio. One's design objective may be to make the assisted leg behave in accordance with a target integral admittance model $X^d_h(s)$, which is defined as:

$$X_h^d(s) = \frac{1}{I_h^d(s^2 + 2\zeta_h^d\omega_{nh}^d s + \omega_{nh}^{d2})} \tag{13}$$

Where $I^d_h$, $\omega^d_{nh}$ and $\zeta^d_h$ are, respectively, the desired values of the inertia moment, natural frequency and damping ratio. The design specifications are formulated in terms of the following parameter ratios:

$$R_\omega \equiv \frac{\omega_{nh}^d}{\omega_{nh}} \text{ (natural frequencies ratio)} \tag{14}$$

$$R_M \equiv \frac{M_h^d}{M_h} \text{ (resonant peak ratio)} \tag{15}$$

$$R_{DC} \equiv \frac{X_h^d(0)}{X_h(0)} \text{ (DC gains ratio)} \tag{16}$$

In (15) $M_h$ and $M^d_h$ are, respectively, the magnitude peaks at resonance for $X_h(j\omega)$ and $X^d_h(j\omega)$. Thus, the design specifications consist of desired values for $R_\omega$, $R_M$ and $R_{DC}$. These specifications are converted into desired values for the dynamic parameters $I^d_h$, $\omega^d_{nh}$ and $\zeta^d_h$ by using the following formulas, which are derived as shown later below:

$$I_h^d = \frac{I_h}{R_{DC}R_\omega^2} \tag{17}$$

$$\omega_{nh}^d = R_\omega\omega_{nh} \tag{18}$$

$$\zeta_h^d = \sqrt{\frac{1-\sqrt{1-4\rho^2}}{2}} \tag{19}$$

where $$\rho = \frac{R_{DC}}{R_M}\zeta_h\sqrt{1-\zeta_h^2} \tag{20}$$

Figure 4A:
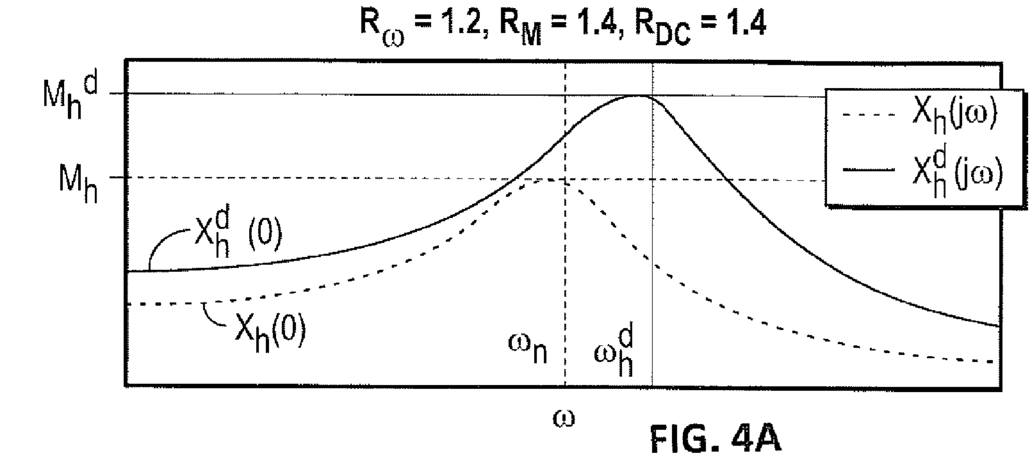
FIG. 4A-4B are illustrative graphs showing frequency responses on an unassisted legs integral admittance ($X_h(j\omega)$) and an exemplary target integral admittance ($X^d_h(j\omega)$) in accordance with one aspect of the present application.
Figure 4B:
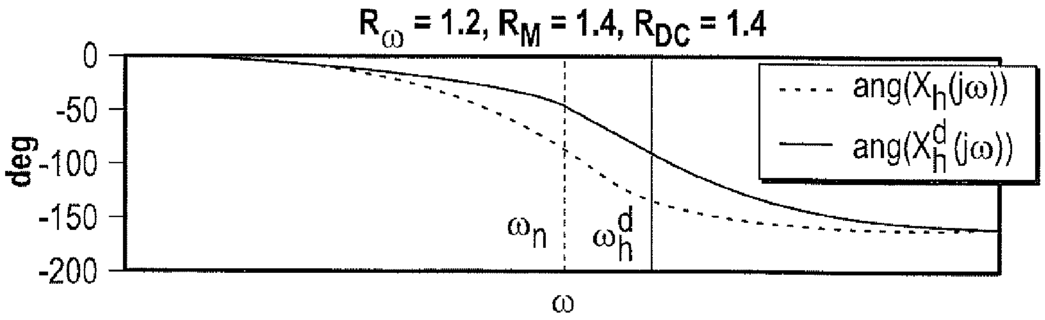

By way of example, FIGS. 4A-4B shows a comparison between the frequency responses of the unassisted leg's integral admittance $X_h(j\omega)$ and a target integral admittance $X^d_h(j\omega)$ with specific values of $R_\omega$, $R_M$ and $R_{DC}$. This particular target response combines several possible assistive effects on the leg: increase in natural frequency, effort reduction at resonance, and gravitational support at low frequencies. In FIGS. 4A-4B, $R_\omega=1.2$, $R_M=1.4$ and $R_{DC}=1.4$. The computed parameters $X^d_h(j\omega)$ are $I^d_h=0.4960$, $\omega^d_{n,h}=1.2$ and $\zeta^d_h=0.1989$.

The task is now to design an exoskeleton control capable of making the leg's dynamic response emulate the target $X^d_h$. To design the exoskeleton control, one may use the linearized model shown in FIG. 5, which represents the human leg coupled to the exoskeleton's arm-actuator assembly (FIG. 1A). The inertias of the leg and the exoskeleton may be coupled by a spring and damper ($k_c$, $b_c$) representing the compliance of the leg muscle tissue combined with the compliance of the exoskeleton's thigh brace. In the diagram, ground represents the exoskeleton's hip brace and may be assumed to be rigid.

$Z_e(s)$ the port impedance of the exoskeleton mechanism. In other words, the impedance felt by the user when the assistive controller is inactive. The magnitude of $Z_e(s)$ should be made as low as possible to ensure that the exoskeleton is backdriveable by the user. The exoskeleton is said to be backdrivable if the motor's output shaft can easily be moved with a relatively small force or torque. This may be accomplished through a combination of mechanical design (i.e., using low inertia components) and an inner-loop control that may compensate the damping and friction in the actuator's transmission. One may assume that such an inner-loop control is already in place, thereby allowing to represent the exoskeleton arm as a pure rotational inertia: $Z_e(s)=I_es$. The exoskeleton and the compliant coupling may be represented as second-order impedance given by:

$$Z_{ec}(s) = I_e s + b_c + \frac{k_o}{s} \tag{21}$$

or, equivalently, $$Z_{ec}(s) = I_e\left(s + 2\zeta_{ec}\omega_{n,ec} + \frac{\omega_{n,ec}^2}{s}\right) \tag{22}$$

where $\omega_{n,ec}$ is the natural frequency of the impedance and where $\zeta_{ec}$ is its damping ratio. In order to reduce the dimensionality of the analysis somewhat, one may assume the impedance (22) to be critically damped, i.e. $\zeta_{ec}=1$. This assumption may be warranted since tests with the SMA device have shown $Z_{ec}(s)$ to be overdamped. Thus, the critically-damped assumption may be conservative as far as stability is concerned. Keeping the analysis in terms of dimensionless frequencies and damping ratios, one may define the following impedance transfer functions:

$$Z_h(s) = Y_h^{-1}(s) = \frac{s^2 + \zeta_h s + 1}{s} \tag{23}$$

$$Z_c(s) = Y_c^{-1}(s) = 2I_e\omega_{n,ec}\left(\frac{s + \frac{\omega_{n,ec}}{2}}{s}\right) \tag{24}$$

$$Z_e(s) = Y_e^{-1}(s) = I_e s \tag{25}$$

Figure 5:
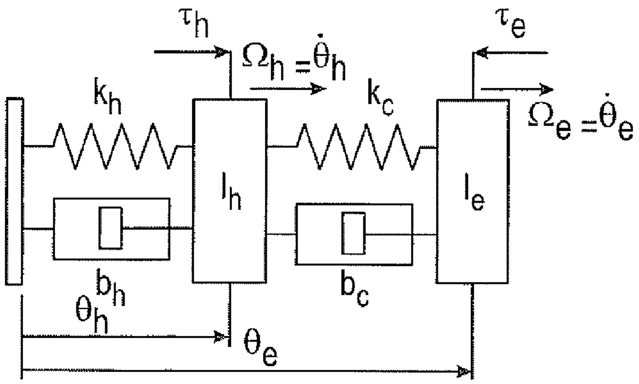
FIG. 5 shows a linear model of an exemplary system formed by the human leg, coupling and exoskeleton device in accordance with one aspect of the present application.

These impedances allow to formulate the dynamics equations of the coupled human-exoskeleton system of FIG. 5 in the Laplace domain.

$$\Omega_h = Y_h(\tau_h - \tau_c) \tag{26}$$

$$\tau_c = Z_c(\Omega_h - \Omega_e) \tag{27}$$

$$\Omega_e = Y_e(\tau_c - \tau_e) \tag{28}$$

where $\tau_c$ is the interaction torque between the leg and the exoskeleton (exerted through the coupling) and $\tau_e$ is the torque generated by a feedback compensator $Z_f(s)$:

$$\tau_e = Z_f\Omega_e \tag{29}$$

$Z_f(s)$ embodies the exoskeleton's assistive control. It should be noted that, although the compensator takes in angular velocity feedback, $Z_f(s)$ may contain derivative or integral terms. Therefore, the physical control implementation may involve feedback of angular acceleration or angular position. Further, while the torque generated by the control is $\tau_e$, the actual torque exerted on the leg by the exoskeleton is $\tau_c$. This means that, per the definitions above, the assistive torque is actually $\tau_c$.

Figure 6A:
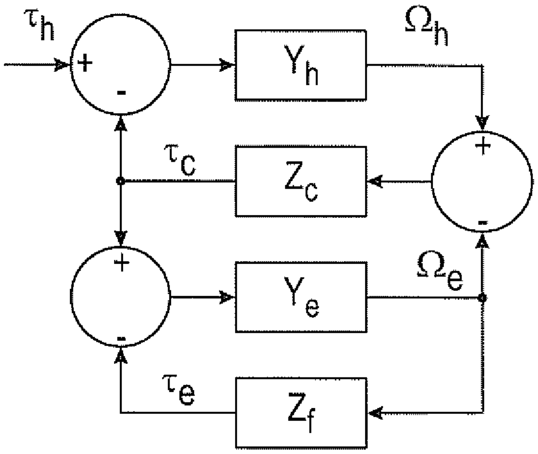
FIG. 6A-6C are illustrative block diagrams of an exemplary system formed by the human leg, coupling and exoskeleton device in accordance with one aspect of the present application.

Using equations (26), (27), (28) and (29), one may represent the coupled leg-exoskeleton system as the block diagram shown in FIG. 6A. The aim of the assistive control is to make the dynamic response of this system such that it matches the frequency response of the target integral admittance $X^d_h(s)$. The present control design may be described as a two-step procedure: (1) Design of an angle feedback compensator to achieve the target DC gain (stiffness and gravity compensation); (2) Design of an angular acceleration feedback compensator to achieve the target natural frequency and target resonant peak. The angular acceleration feedback compensator is designed using a pole placement technique to ensure the stability of the coupled system.

Decoupling the DC gain problem from the other two is valid because, as may be seen on FIG. 2, the DC gain is only affected by a stiffness perturbation, which may easily be implemented via angular feedback. The same figure suggests that the natural frequency target may be achieved by either an angle feedback (stiffness perturbation) or angular acceleration feedback (inertia perturbation). By choosing an angular acceleration feedback, one may avoid creating a conflict with the DC gain objective, which depends exclusively on angle feedback. Furthermore, one may show that employing an angular acceleration feedback compensator with sufficient degrees of freedom may allow one to achieve the natural frequency and resonant peak targets simultaneously.

The design of the compensator for target DC gain is a simple application of the dynamics of the coupled system in the static (zero frequency) case. From FIG. 5, the torque balance on the human leg's inertia $I_h$ yields:

$$k_h\theta_h = \tau_h - \tau_c \tag{30}$$

Torque balance on the exoskeleton's inertia $I_e$ yields:

$$\tau_c - \tau_e = 0 \tag{31}$$

Since the objective is to compensate for the stiffness and gravitational torque acting on the leg, the assistive torque may be provided by a virtual spring:

$$\tau_e = k_{DC}\theta_e \tag{32}$$

If one were to assume that for the coupling to have sufficient stiffness that $\theta_e \approx \theta_h$, from equation (30), the net muscle torque becomes:

$$\tau_h = k_h\theta_h - k_{DC}\theta_e \cong (k_h - k_{DC})\theta_h \tag{33}$$

To determine the virtual spring stiffness $k_{DC}$, we refer to the equations listed below. Equation (69) defines an intermediate target integral admittance $X_{h,DC}(s)$, embodying the DC gain specification. Maintaining the assumption that $\theta_e \approx \theta_h$, one may note that $X_{h,DC}(s)$ may be implemented by adding the virtual spring to the human leg's impedance. Thus an alternative definition is:

$$\hat{X}_{h,DC}(s) = \frac{1}{I_h s^2 + 2I_h\zeta_h\omega_{nh}s + I_h\omega_{nh}^2 + k_{DC}} \tag{34}$$

Making $X_{h,DC}(0) = X_{h,DC}(0)$ yields:

$$I_h\omega_{nh}^2 + k_{DC} = I_h\omega_{nh,DC}^2 \tag{35}$$

But from (71) below, we have $\omega^2_{nh,DC} = R^{-1}_{DC}\omega^2_{nh}$. Thus, the stiffness and gravity compensation gain are:

$$k_{DC} = I_h\omega_{nh}^2(R_{DC}^{-1} - 1) \tag{36}$$

Combining the angular position feedback (32) with the computed value $k_{DC}$ generates the following closed-loop exoskeleton admittance:

$$Y_{e,DC} = \frac{Y_e}{1 + \frac{k_{DC}}{s}Y_e} \tag{37}$$

For the DC gain specification of $R_{DC} < 1$, we have $k_{DC} < 0$, i.e. positive feedback of the angular position. As a consequence, the closed-loop exoskeleton admittance has a pole at $s = +\sqrt{k_{DC}I_e^{-1}}$, which makes the isolated exoskeleton unstable. However, the coupled system formed by the leg and the exoskeleton will be stable if the virtual stiffness coefficient of the assisted leg remains positive.

With the compensator for the target DC gain in place, the forthcoming analysis focuses on the target admittance for the assisted leg given by $Y^d_h(s) = sX^d_h(s)$. The objective is to design a compensator capable of increasing the natural frequency of the leg as well as the magnitude peak of its admittance. For the aforementioned objective, when designing the controller, one may need to take into account designing for both performance and stability. Although, one may want to control the relationship between the human muscle torque $\tau_h$ and the leg's angular velocity $\Omega_h$ to match $Y^d_h(s)$, the present design will focus on the transfer function relating $\tau_h$ to the exoskeleton angular velocity $\Omega_e$, as this may be the only practical way of measuring $\Omega_e$. This may be acceptable under the assumption that the coupling is sufficiently rigid and therefore $\Omega_e \approx \Omega_h$.

Figure 6B:
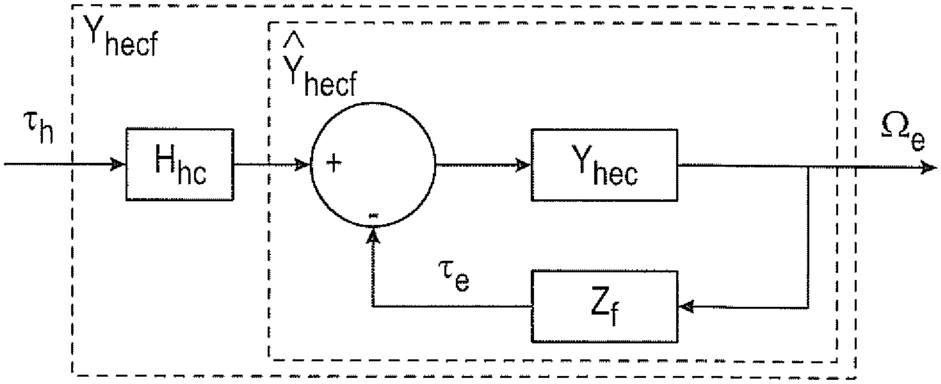

One may begin by substituting $Y_e(s)$ with $Y_{e,DC}$ (s) in FIG. 6A and converting the block diagram using the system's loop transfer function. FIG. 6B shows the equivalent block diagram, which contains the following transfer functions:

$$Y_{hec}(s) = \frac{N_{hec}(s)}{D_{hec}(s)} = \frac{Z_h + Z_c}{Z_h Z_{e,DC} + Z_c Z_{e,DC} + Z_c Z_h} \quad (38)$$

where $Z_{e,DC} = Y_{e,DC}^{-1}$, and $$H_{hc}(s) = \frac{Z_c}{Z_h + Z_c} = \frac{Z_c}{N_{hec}(s)} \quad (39)$$

From FIG. 6B, one may define the closed-loop transfer function:

$$\hat{Y}_{hecf}(s) = \frac{Y_{hec}}{1 + Z_f Y_{hec}} = \frac{N_{hec}}{D_{hec} + Z_f N_{hec}} \quad (40)$$

and, the transfer function relating the human torque to the encoder angular velocity:

$$Y_{hecf}(s) = \frac{\Omega_e(s)}{\tau_h(s)} = H_{hc}(s)\hat{Y}_{hecf}(s) = \frac{Z_c}{D_{hec} + Z_f N_{hec}} \quad (41)$$

From linear feedback control theory, the dynamic response properties of $Y_{hecf}(s)$ may be determined mainly by its characteristic polynomial. Therefore, one may formulate the design of the compensator $Z_f(s)$ as a pole placement problem, namely, to make the dominant poles of $\hat{Y}_{hecf}(s)$ match the poles of the target admittance $Y^d_h(s)$. Because $Y_{hecf}(s)$ and $\hat{Y}_{hecf}(s)$ share the same characteristic polynomial, the present design uses the standard tools of root locus and Bode stability applied to the loop transfer function of $\hat{Y}_{hecf}(s)$.

We define the loop transfer function, $L_{hecf}(s)$, as a ratio of monic polynomials obeying:

$$K_L L_{hecf}(s) = Z_f(s) Y_{hec}(s) \quad (42)$$

where $K_L$ is the loop gain. Referring to FIG. 6B, the product $H_{hc}(s)Y_{hec}(s)$ may be considered the "baseline" admittance of the coupled human-exoskeleton system, i.e. the admittance in the absence of assistive control.

Given that $Y_{hec}(s)$ may already incorporate positive feedback of the angular position (through $Z_{e,DC}$), one may want to analyze its stability and passivity properties before designing the assistive control $Z_f(s)$. For this analysis, one may use the dimensionless moment of inertia of the SMA arm and actuator assembly, $I_e$. One may begin by writing the impedances in (38) in terms of polynomial ratios and gains:

$$Z_h(s) = \frac{N_h(s)}{s} = \frac{s^2 + \zeta_h s + 1}{s} \quad (43)$$

$$Z_c(s) = z_{co}\frac{N_c(s)}{s} = 2I_e\omega_{n,ec}\left(\frac{s + \frac{\omega_{n,ec}}{2}}{s}\right)$$

$$Z_{e,DC}(s) = I_e\frac{N_e(s)}{s} = I_e\left(\frac{s^2 + \frac{k_{DC}}{I_e}}{s}\right)$$

This in turn yields $Y_{hec}(s)$ as the following ratio of polynomials:

$$Y_{hec}(s) = \frac{s(N_h + z_{co}N_c)}{I_e N_e N_h + z_{co}N_e N_c + z_{co}N_h} \quad (44)$$

or $$Y_{hec}(s) = \frac{1}{I_e} L_{hec}(s) \quad (45)$$

where $L_{hec}(s)$ is a ratio of monic polynomials. From inspection of (43) and (44), $Y_{hec}(s)$ has four poles and three zeros, including one zero at the origin.

Figure 7A:
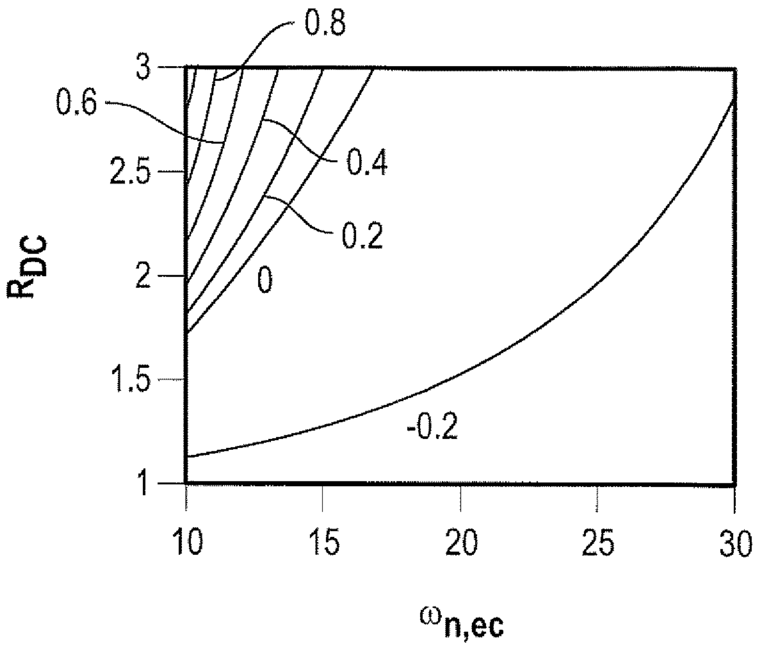
FIG. 7A is an illustrative contour plot showing the real part of the dominant poles of $Y_{hec}(s)$ (where $Y_{hec}(s)$ is defined as the admittance of the coupled system formed by the leg and the exoskeleton in the absence of the exoskeleton's assistive control), as a function of the DC gain ratio $R_{DC}$ and the coupling's natural frequency, $\omega_{n,ec}$ in accordance with one aspect of the present application.

FIG. 7A shows contour plots of the real part of the dominant poles of $Y_{hec}(s)$ as a function of $R_{DC}$ and the natural frequency of the coupling, $\omega_{n,ec}$. One may observe that for most values of $R_{DC}$ and $\omega_{n,ec}$, the dominant poles' real part are constant and equal to −0.2. Only for combinations of very low natural frequency of the coupling, and high values of DC gain ratio, do the dominant poles cross over to the right-hand side of the complex plane (RHP).

For now one may maintain the assumption that the $R_{DC}$ specification does not violate the stability of $Y_{hec}$. Ensuring that $Y_{hec}$ has no RHP or imaginary poles guarantees the existence of a range of negative loop gains $K_L$ for which the closed-loop transfer function $\hat{Y}_{hecf}(s)$ of is stable.

Figure 7B:
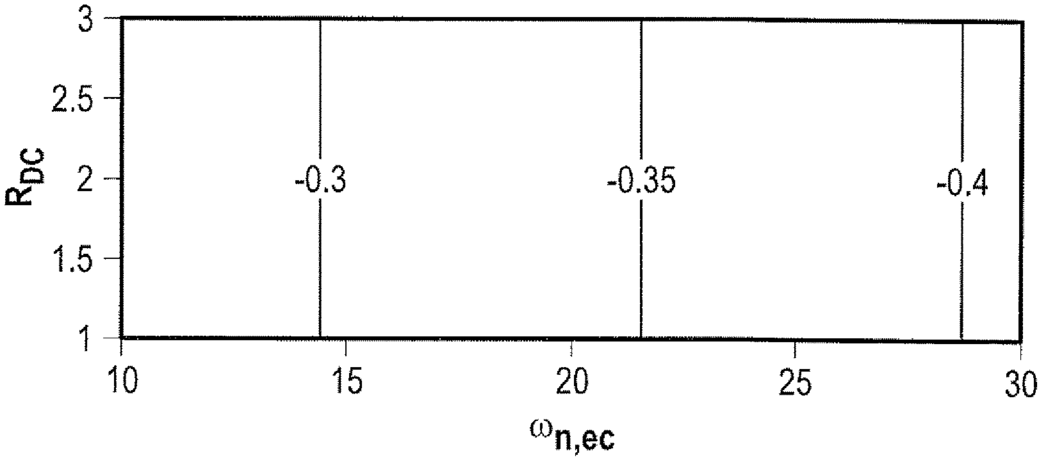
FIG. 7B is an illustrative graph showing maximum real part of the zeros of $Y_{hec}(s)$, excluding the zero at the origin, as a function of the DC gains ratio $R_{DC}$ and the natural frequency $\omega_{n,ec}$ of the exoskeleton with arm-leg coupling, in accordance with one aspect of the present application.
Figure 8A:
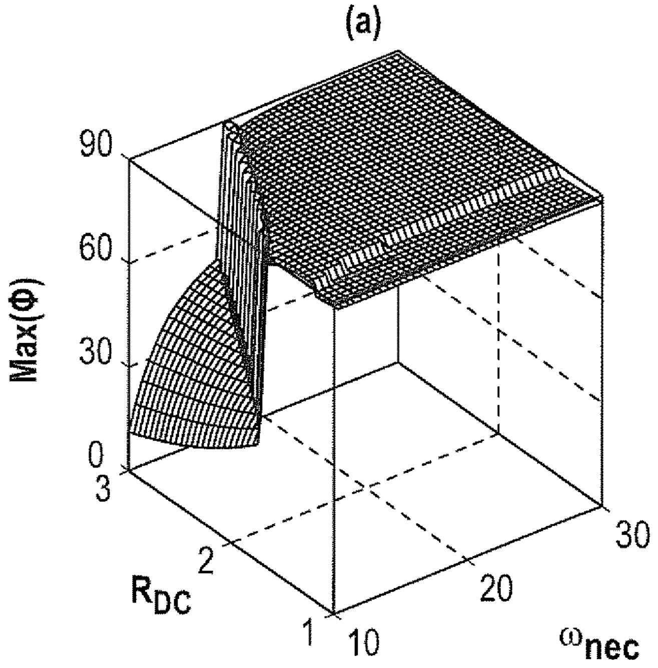
FIG. 8A-8B show illustrative frequency responses of $Y_{hec}(j\omega)$ as a function of $R_{DC}$ and $\omega_{n,ec}$ in accordance with one aspect of the present application.
Figure 8B:
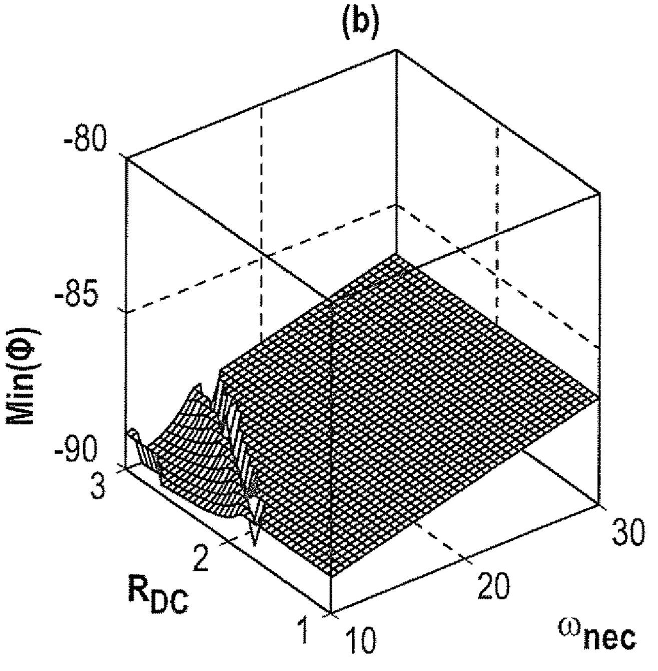
Figure 9A:
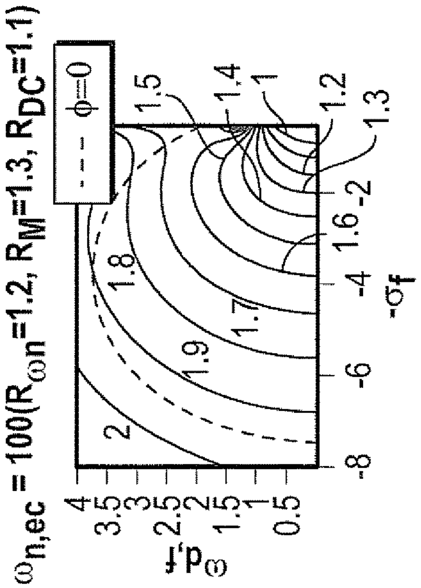
FIG. 9A-9D shows illustrative plots of phase property and gain margins of the exemplary coupled system formed by the human limb, the exoskeleton and the compensator with positive feedback in accordance with one aspect of the present application.
Figure 9B:
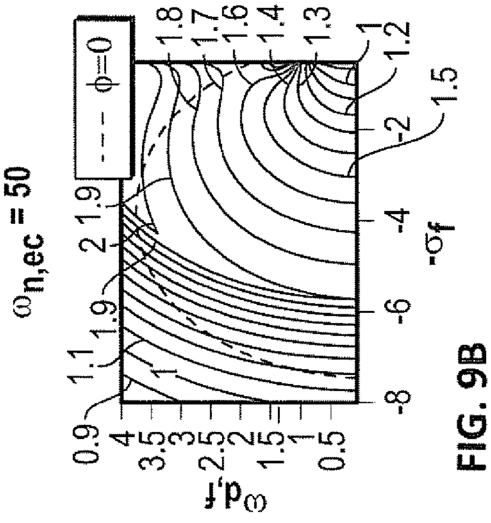
Figure 9C:
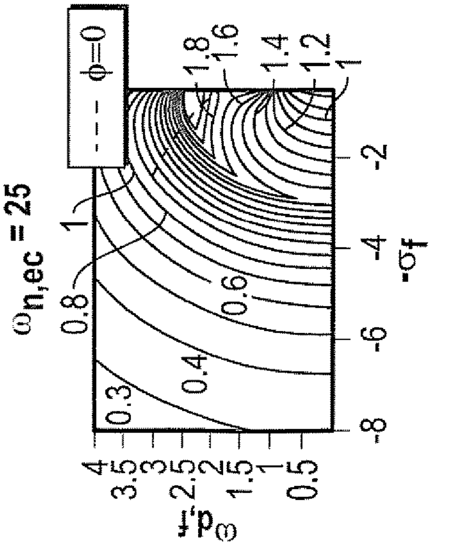
Figure 9D:
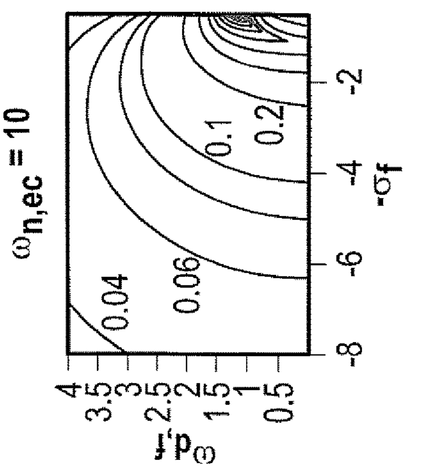

One may note that the maximum real part of the zeros of $Y_{hec}(s)$ (excluding the zero at the origin) is always negative, i.e. $Y_{hec}(s)$ is a minimum phase system (FIG. 7B). Recalling the passivity conditions given above, one may obtain the extreme values of the phase of the frequency response of $Y_{hec}(j\omega)$ for the range of values of $R_{DC}$ and $\omega_{n,ec}$ previously tested. FIGS. 8A-8B show that the phase value remains within −90° and 90°, which means that the stable $Y_{hec}(s)$ is also be passive. Thus, the coupled human exoskeleton system in baseline state ($H_{hc}(s)Y_{hec}(s)$) is passive as well. This may be a valuable result since it means that in the baseline state the system may not run the risk of becoming unstable when entering in contact with any passive environments (Colgate, J., Hogan, N. "An analysis of contact instability in terms of passive physical equivalents." Proceedings of the IEEE International Conference on Robotics and Automation (1989) pp 404-409), for example during ground contact.

In order to explain the derivation of the feedback compensator $Z_f(s)$ for natural frequency and resonant peak targets, one may use a specific design example involving the Honda SMA device disclosed above. As an example, one may set forth the following design specifications: $R_\omega$=1.2, $R_M$=1.3 and $R_{DC}$=1.1. These in turn yield a set of parameter values for the target integral admittance ($I^d_h$, $\omega^d_{nh}$ and $\zeta^d_h$). Given these values, the desired locations of the dominant poles, $p_h^d$, are computed as:

$$p^d_h = -\sigma^d_h + j\omega^d_{dh} \quad (46)$$

$$\bar{p}^d_h = -\sigma^d_h - j\omega^d_{dh}$$

where $$\sigma^d_h = \zeta^d_h \omega^d_{nh}$$

$$\omega^d_{dh} = \omega^d_{nh}\sqrt{1 - \zeta^{d2}_h}$$

The gain of the feedback compensator for target DC gain, $k_{DC}$, is computed with (36).

As disclosed above, an increase in natural frequency may be accomplished by compensating the inertia of the second-order system. This may be accomplished by employing positive acceleration feedback in the present compensator. However, unfiltered acceleration feedback may not satisfy the present design requirements. For a compensator defined simply as $Z_f(s)\equiv I_c s$, the stability limit of the inertia compensation gain is $I_c=-I_e$. In other words, the best such a compensator may be able to do before causing instability is to cancel the exoskeleton's own inertia but none of human leg's inertia.

In order to overcome the limitations of pure positive acceleration feedback, one may add a pair of complex conjugate poles $-\sigma_f \pm j\omega_{d,f}$ to the compensator. Therefore the present proposed feedback compensator model is:

$$Z_f(s) \equiv -I_c s \frac{\sigma_f^2 + \omega_{d,f}^2}{s^2 + 2\sigma_f s + \sigma_f^2 + \omega_{d,f}^2} \tag{47}$$

where $\sigma_f$ and $\omega_{d,f}$ are parameters the values of which have be determined. With $Z_f(s)$ thus defined, and recalling (42), the loop transfer function becomes:

$$L_{hecf}(s) = \frac{sL_{hec}(s)}{s^2 + 2\sigma_f s + \sigma_f^2 + \omega_{d,f}^2} \tag{48}$$

Thus, given a loop gain $K_L<0$ that meets the design requirements, the inertia compensation gain is:

$$I_c = \frac{K_L I_e}{\sigma_f^2 + \omega_{d,f}^2} \tag{49}$$

In the present compensator model, $\sigma_f$ and $\omega_{d,f}$ provide two degrees of freedom with which to shape the positive feedback root locus $L_{hecf}(s)$. Shaping the root locus pursues two different objectives: (1) Making the root locus pass through locations of the dominant poles, $p^d_h$ and $p^{-d}_h$ or as close to them as possible. Thus, with an appropriate gain $I_c$, the system's closed-loop transfer function $\hat{Y}_{hecf}(s)$ (FIG. 6B) will have poles at or near, $p^d_h$ and $p^{-d}_h$. (2) Maximizing the stability margins of $\hat{Y}_{hecf}(s)$ to ensure that the design solution provided by $\sigma_f$, $\omega_{d,f}$ and $I_c$ is stable. It may be noted that, with positive feedback, while two of the closed-loop poles of $\hat{Y}_{hecf}(s)$ satisfy $s=p^d_h$, any of the remaining poles may cause instability. As explained below, the present compensator design avoids this risk by maximizing the stability margins of the coupled system.

The present compensator design solves a pole placement problem, namely finding values of $\sigma_f$, $\omega_{d,f}$ and $I_c$, such that $\hat{Y}_{hecf}(s)$ may have poles at $p^d_h$ and $p^{-d}_h$. One may refer to $\{\sigma_f, \omega_{d,f}$ and $I_c\}$ as a candidate solution. When the candidate solution generates stability of the coupled system, it may be considered a valid compensator design. Solutions for the pole placement problem may be found by applying the properties of the positive-feedback root locus as follows. (a) Phase property: for $s=p^d_h$ the phase $\Phi$ of $L_{hecf}(s)$ should be equal to zero. One may express this condition as:

$$\Phi=\Phi(\sigma_f,\omega_{d,f},p^d_h)=\angle L_{hecf}(s)=0 \tag{50}$$

which yields a range of solutions for $\sigma_f$ and $\omega_{d,f}$. (b) Gain property: for $s=p^d_h$ the loop gain $K_L$ satisfies:

$$K_L=K_L(\sigma_f,\omega_{d,f},p_h^d)=-1/|L_{hecf}(p_h^d)| \tag{51}$$

Given a solution pair $\{\sigma_f, \omega_{d,f}\}$ and the value of $K_L$ resulting from (51), the inertia compensation gain $I_c$ is computed using (49).

The formulas for computing $\Phi$ and $K_L$ are given, respectively, by (81) and (83). Assuming $\sigma_f>0$, the stability of the candidate solution $\{\sigma_f, \omega_{d,f}, I_c\}$ depends on the value of $I_c$. Thus, if one defines $I_{c,M}$ as the inertia compensation gain that puts the closed-loop system at the threshold of stability for given values of $\sigma_f$ and $\omega_{d,f}$, the stability condition is:

$$R_{I_c} \equiv \frac{I_{c,M}}{I_c} > 1 \tag{52}$$

In order to compute $R_{Ic}$, the loop gain at the instability threshold is:

$$K_{L,M} = \frac{-1}{|L_{hecf}(j\omega_M)|} \tag{53}$$

where $$\omega_M = \omega \mid \angle(-L_{hecf}(j\omega)) = -180^\circ \tag{54}$$

This allows computing the ratio of inertia compensation gains simply as:

$$R_{I_c} = \frac{I_{c,M}}{I_c} = \frac{K_{L,M}}{K_L} \tag{55}$$

$R_{Ic}$ constitutes a stability margin, to be precise, a gain margin. Therefore it may play an important role in the design of the compensator.

One may need to consider that the values of the system's parameters may involve considerable uncertainty, especially in the case of the human leg and the coupling. Aside from its implications on performance, parameter uncertainty may pose the risk of instability. Thus, the physical coupled system may be unstable even though the compensator is theoretically stabilizing. To minimize that risk, one may propose formulating the design of the compensator as a constrained optimization problem: given the target dominant pole $s=p^d_h$, to find a combination $\{\sigma_f, \omega_{d,f}, I_c\}$ that maximizes the inertia compensation gains ratio $R_{Ic}$ while preserving the phase condition (50).

Thus, one may formulate the feedback compensator design problem as follows: given a target dominant pole $p^d_h$ find:

$$\max_{\{\sigma_f,\omega_{d,f}\}} R^2_{I_c}(\sigma_f, \omega_{d,f}, p^d_h) \tag{56}$$

$$\text{Subject to } \Phi(\sigma_f, \omega_{d,f}, p^d_h) = 0$$

The complete design procedure of the assistive control for admittance shaping may be summarized thus: 1. Formulate the design specifications $R_\omega$, $R_M$ and $R_{DC}$. 2. With the DC gain specification $R_{DC}$, compute the angular position feedback gain $k_{DC}$ using (36). 3. Compute the target admittance parameters $\omega^d_{nh}$ and $\zeta^d_h$ using (18) and (19). 4. Obtain the dominant pole of the target admittance as $p_h^d=\sigma_h^d+j\omega_{dh}^d$ using (46). 5. Obtain the parameters $\{\sigma_f, \omega_{d,f}\}$ of the feedback compensator $Z_f(s)$ (47) $b_y$ performing the constrained optimization (56). 6. With $\{\sigma_f, \omega_d\}$ obtain the loop gain $K_L$ using (83) and the inertia compensation gain $I_c$ using (49).

Figure 10A:
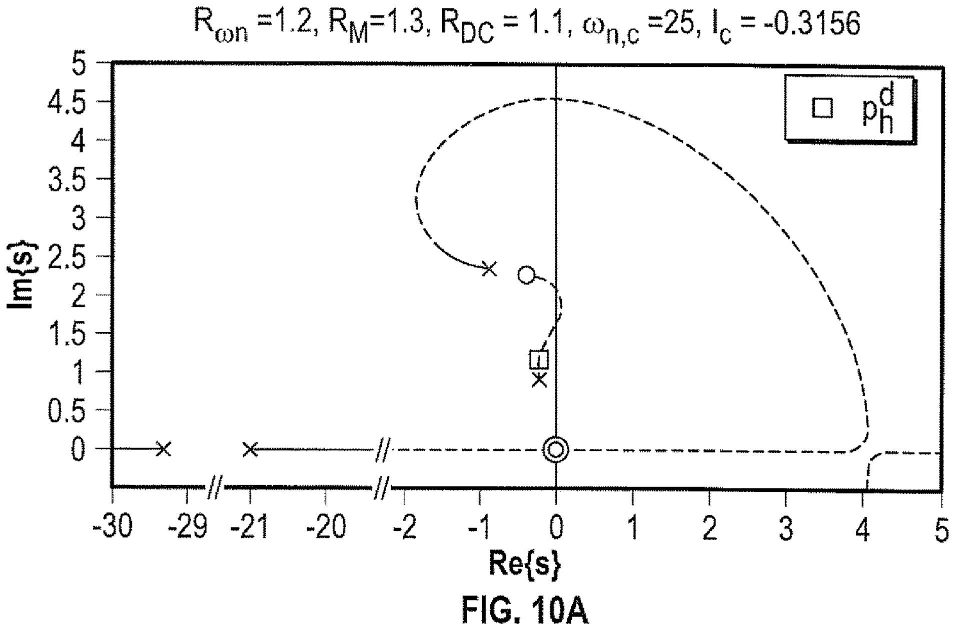
FIG. 10A shows an exemplary positive-feedback root locus of $L_{hecf}(s)$ (where $L_{hecf}(s)$ is the loop transfer function of the coupled system formed by the leg, the exoskeleton and the exoskeleton's assistive control) in accordance with one aspect of the present application.
Figure 10B:
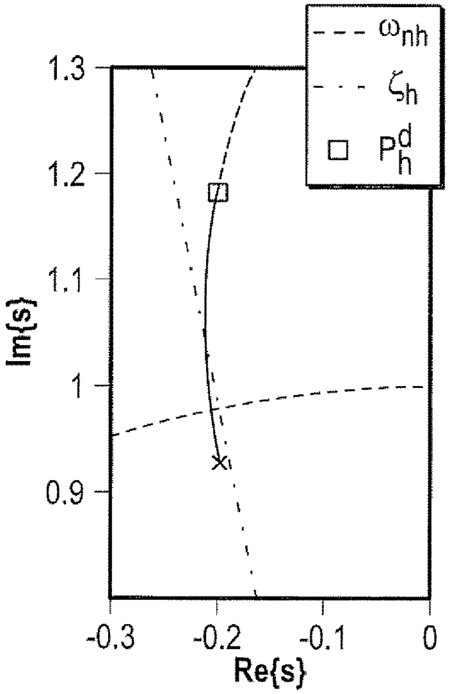
FIG. 10B shows exemplary details of the root locus wherein the root locus passes through the target location of the dominant pole, $p^d_h$ in accordance with one aspect of the present application.
Figure 10C:
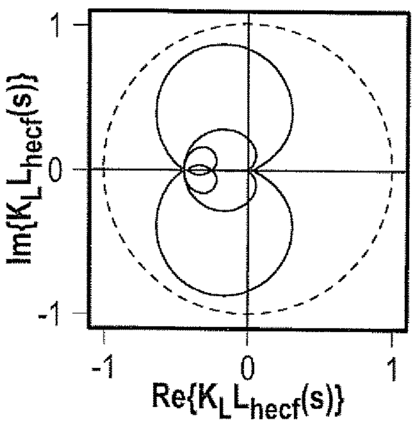
FIG. 10C shows an exemplary Nyquist plot for the loop transfer function $L_{hecf}(s)$ times the computed feedback gain $K_L$, in accordance with one aspect of the present application.
Figure 11C:
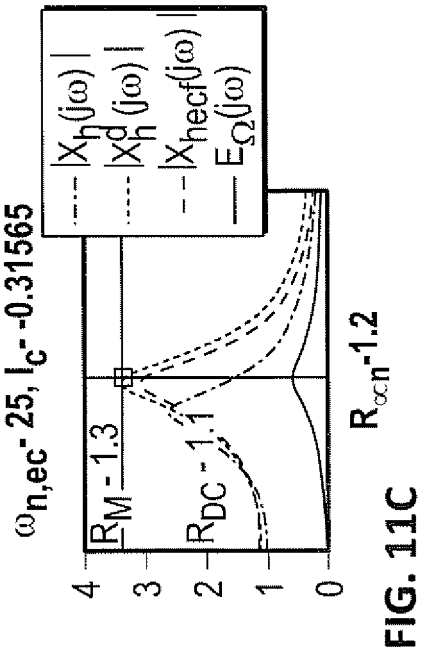
FIG. 11A-11D shows illustrative frequency responses of the integral admittance of the human-exoskeleton system with feedback compensator ($X_{hecf}(s)$) in accordance with one aspect of the present application.
Figure 11D:
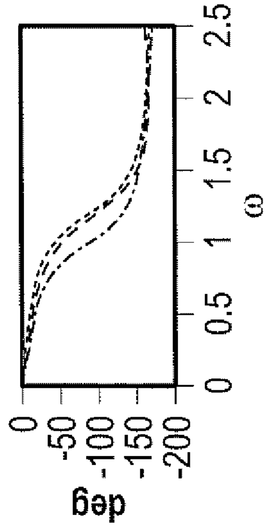
Figure 11A:
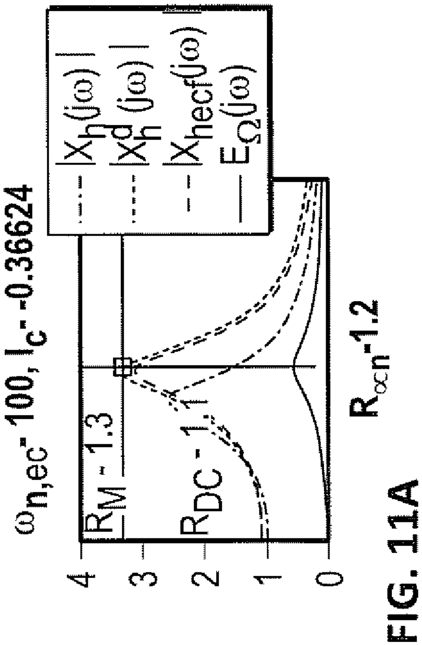
Figure 11B:
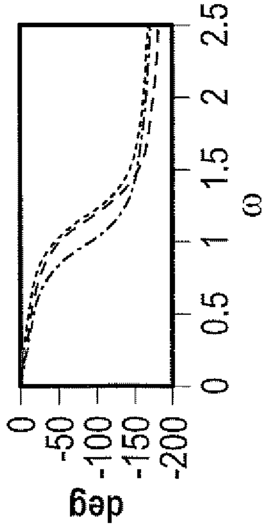

Compensator designs may be generated for different values of coupling stiffness. For example, FIGS. 10A and 10B show the positive-feedback root locus of $L_{hecf}(s)$ for the coupling with $\omega_{n,ec}=25$. These figures illustrate the fact that it is possible to find compensator solutions that achieve the pole placement objective, despite the fact that positive feedback tends to destabilize the coupled system (as indicated by the incursions of the root locus into the RHP as $K_L \rightarrow -\infty$). The solution obtained may possess a degree of robustness, as indicated by the Nyquist plot of FIG. 10C. Thus in principle it may be possible for the coupled system to maintain stability in spite of discrepancies between the system's model and the actual properties of the physical leg and exoskeleton.

The present design goal is to make the dynamic response of the exoskeleton-assisted leg match the integral admittance model $X^d_h(s)$ (13) as closely as possible. FIGS. 11A-11D shows a comparison between the frequency response of the coupled system's integral admittance $X_{hecf}(s)$ and the response of the model $X^d_h(s)$. The frequency response of the unassisted leg (modeled by $X_h(s)$) may be seen for reference. It may be seen that the response of the coupled system closely matches that of the model despite the differences of order among the transfer functions. $X^d_h(s)$ only has two poles, whereas $X_{hecf}(s)$ has six poles and four zeros.

Below, one may examine the stability robustness of the exoskeleton's control to variations in the parameters of the coupled system. One may focus on the two parameters that may have the most direct affect on the stability of the system, namely the stiffness of the human leg's joint and the stiffness of the coupling. The robustness analysis may in turn yield some guidelines for the estimation of these parameters.

The present robustness analysis assumes the exoskeleton model $Z_e$ to be sufficiently accurate and focus on the two system parameters that may be difficult to identify, the stiffness of the human leg's joint and the stiffness of the coupling. While the stiffness of the hip joint may be estimated with moderate accuracy under highly controlled conditions (Fee, J., Miller, F. "The leg drop pendulum test performed under general anesthesia in spastic cerebral palsy." Developmental Medicine and Child Neurology (2004) 46: pp 273-2), in practice it may be subject to variations due to co-activation of the hip-joint muscles. The stiffness of the coupling between the leg and the exoskeleton may depend not only on the thigh brace but also on the compliance of the thigh tissue, which may be a highly uncertain quantity. At a minimum, one should analyze the stability of the system under variations of these two parameters.

Figure 6C:
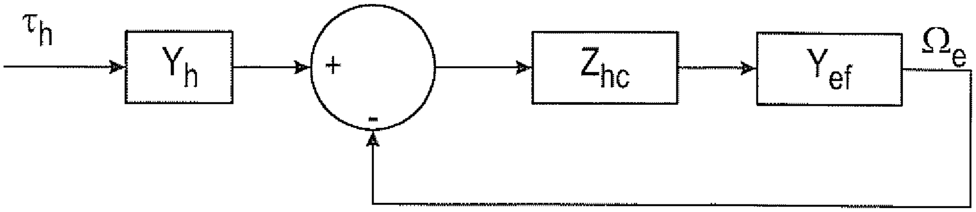

One may begin by converting the system's block diagram in FIG. 6A to the equivalent form of FIG. 6C. In this diagram, the parameters of the human limb and the coupling may be bundled together in the transfer function $Z_{hc}$, defined as:

$$Z_{hc}(s)=Y_{hc}^{-1}(s)=(Y_h+Y_c)^{-1} \tag{57}$$

One may use the transfer function defined above to analyze the effects of uncertainties in the stiffness of the human leg's joint and the stiffness of the coupling. The other transfer function in the feedback loop, $Y_{ef}$, which combines the parameters of the exoskeleton and the feedback compensator, is defined as:

$$Y_{ef}(s)=Z_{ef}^{-1}(s)=(z_e+z_f)^{-1} \tag{59}$$

One may consider the exoskeleton-compensator system $Y_{ef}(s)$ to provide robust stability if it stabilizes the closed-loop system of FIG. 6C for a reasonably large range of variations in the uncertain parameters. To this end one may define the system's nominal closed-loop transfer function, $S_{hecf}(s)$ as:

$$S_{hecf}(s) = \frac{Z_{hc}Y_{ef}}{1+Z_{hc}Y_{ef}} = \frac{1}{1+Y_{hc}Z_{ef}} \tag{60}$$

The perturbed closed-loop transfer function $\tilde{S}_{hecf}(s)$ may be defined by substituting $Y_{hc}$ in (59) with a transfer function:

$$\tilde{Y}_{hc}=\tilde{Y}_h+\tilde{Y}_c \tag{61}$$

which contains the parameter uncertainties. This in turn leads to the following expression:

$$\tilde{S}_{hecf}(s) = \frac{\left(\frac{Y_{hc}}{\tilde{Y}_{hc}}\right)S_{hecf}}{1+\left(\frac{Y_{hc}}{\tilde{Y}_{hc}}-1\right)S_{hecf}} \tag{62}$$

Thus the perturbed system may be stable if the characteristic equation of (62) has no roots in the RHP.

One may define $\delta k_h$ as the uncertainty in the hip-joint stiffness value and $\delta k_c$ as the uncertainty in the coupling stiffness value. In order to study the dependency of the system's stability on $\delta k_h$ and $\delta k_c$, one may use the following intermediate expressions:

$$Y_h = \frac{s}{D_h},\ \tilde{Y}_h = \frac{s}{\tilde{D}_h},\ Y_c = \frac{s}{D_c},\ \tilde{Y}_c = \frac{s}{\tilde{D}_c} \tag{63}$$

where $$\begin{aligned} D_h &= I_h s^2 + b_h s + k_h, \\ \tilde{D}_h &= D_h + \delta k_h \\ D_c &= b_c s + k_c, \\ \tilde{D}_c &= D_c + \delta k_c \end{aligned} \tag{64}$$

and $$\frac{Y_{hc}}{\tilde{Y}_{hc}} = \frac{\tilde{D}_h\tilde{D}_c(D_h+D_c)}{D_hD_c(\tilde{D}_h+\tilde{D}_c)} \tag{65}$$

Substituting (65) in (62), one may arrive at the following equivalent expressions for the characteristic equation of (62):

$$\begin{aligned} &1+\delta k_h W_h(s) = 0 \text{ for } \delta k_h \neq 0,\ \delta k_c = 0 \\ &1+\delta k_c W_c(s) = 0 \text{ for } \delta k_h = 0,\ \delta k_c \neq 0 \end{aligned} \tag{66}$$

where $$\begin{aligned} W_h(s) &= \frac{D_h + D_cS_{hecf}}{D_h(D_h+D_c)} \\ W_c(s) &= \frac{D_c + D_hS_{hecf}}{D_c(D_h+D_c)} \end{aligned} \tag{67}$$

The stability robustness of the system to variations in hip-joint stiffness may be analyzed by applying the Nyquist stability criterion to the open-loop transfer function $\delta k_h W_h(s)$. If $\delta k_h$ has a feasible range of variation $[\delta k_{h,min}, \delta k_{h,max}]$, the Nyquist plots for $\delta k_{h,min} W_h(s)$ and $\delta k_{h,max} W_h(s)$ may represent the critical cases for stability, i.e. the cases in which the Nyquist plot is closest to the critical point −1. In a like manner, the robustness to variations in coupling stiffness may be determined from the open-loop transfer function $\delta k_c W_c(s)$.

Figure 12A:
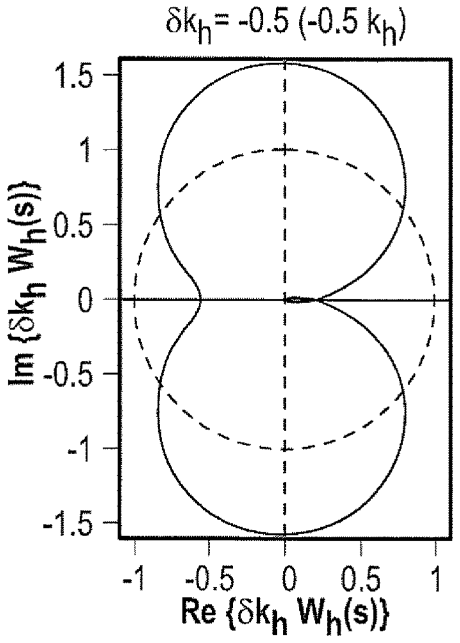
FIG. 12A-12D show illustrative Nyquist plots for the analysis of the stability robustness of the exemplary human-exoskeleton system in accordance with one aspect of the present application.
Figure 12B:
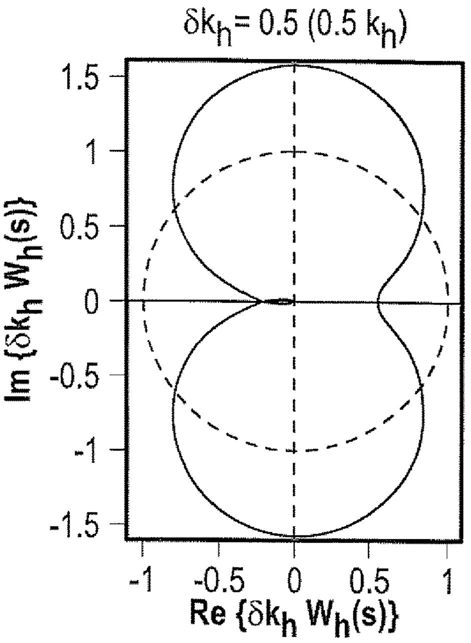
Figure 12C:
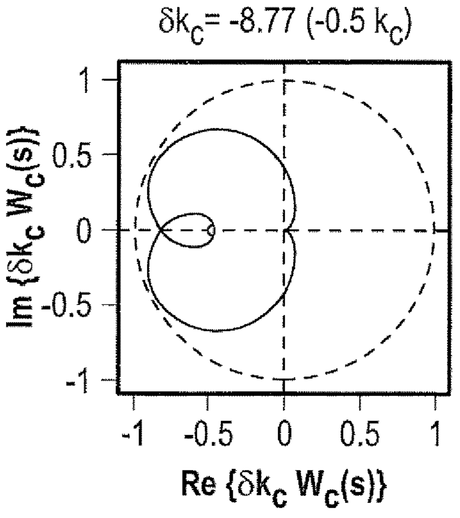
Figure 12D:
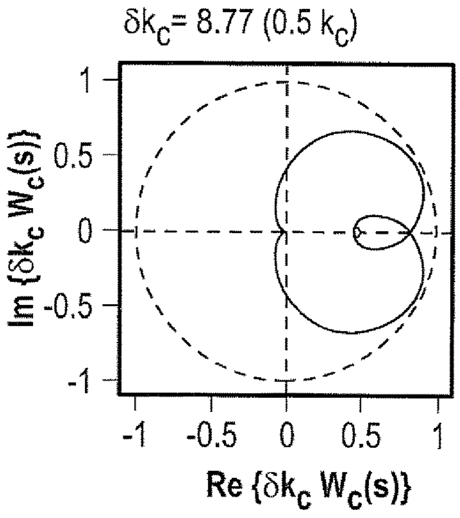
Figure 13A:
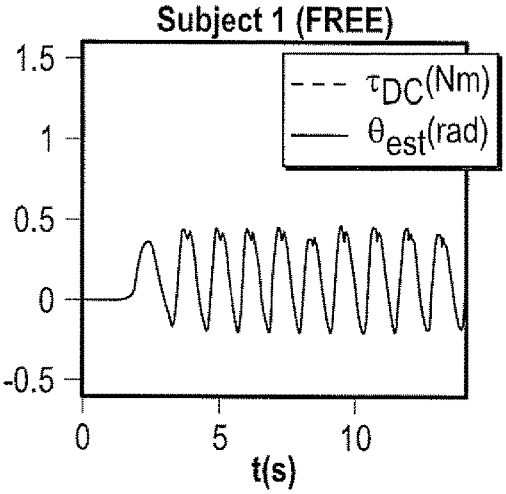
FIG. 13A-13L shows illustrative graphs providing test data of the exemplary human-exoskeleton system in accordance with one aspect of the present application.
Figure 13B:
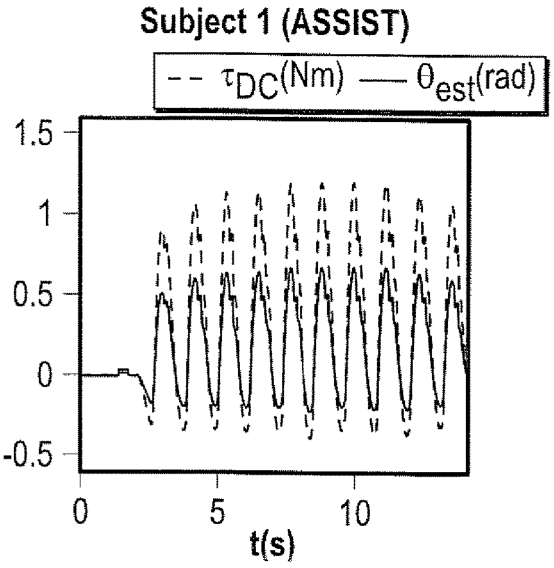
Figure 13C:
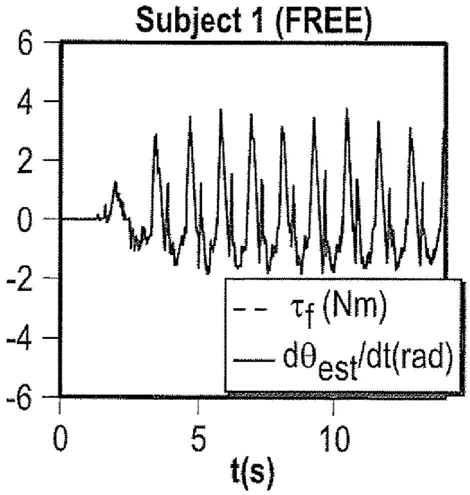
Figure 13D:
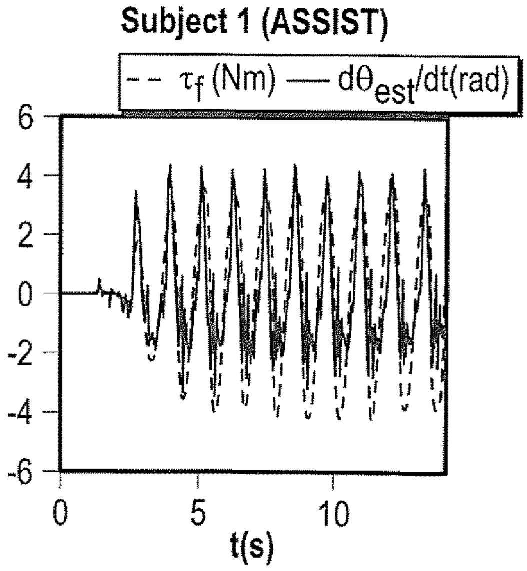
Figure 13E:
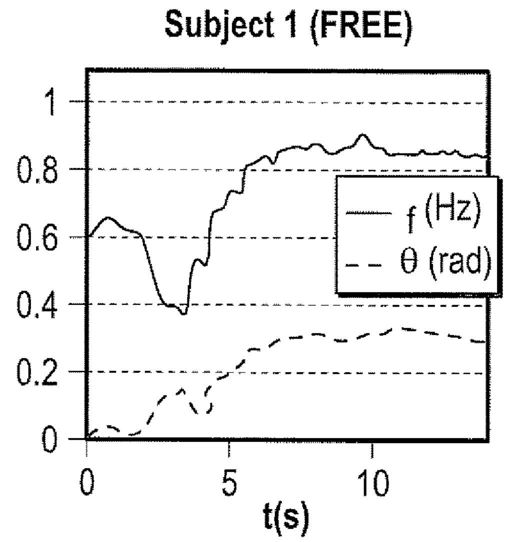
Figure 13F:
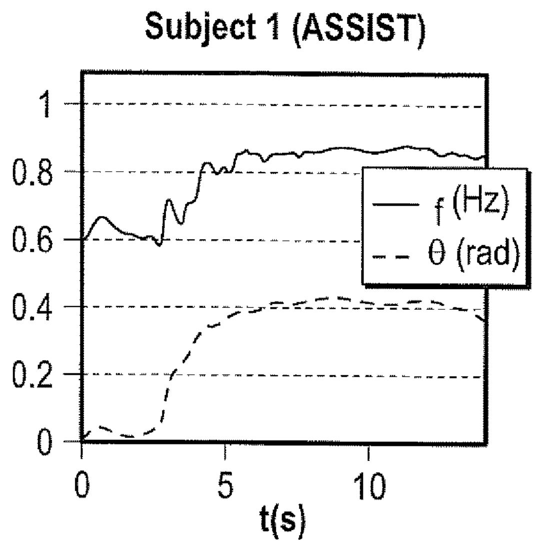
Figure 13G:
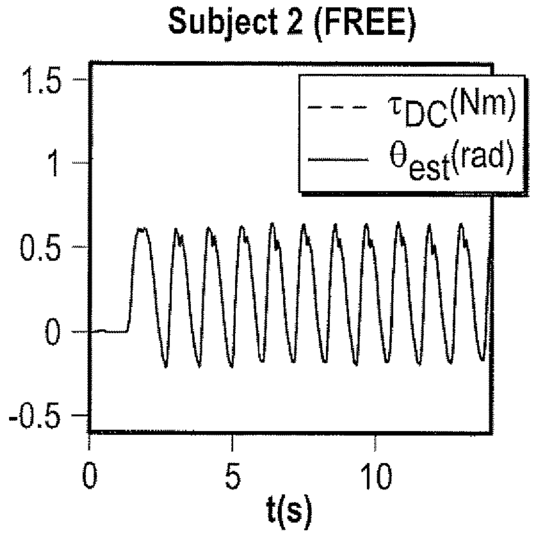
Figure 13H:
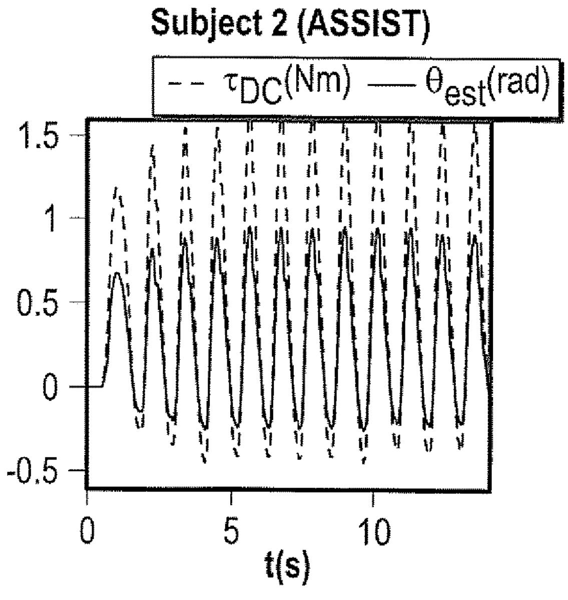
Figure 13I:
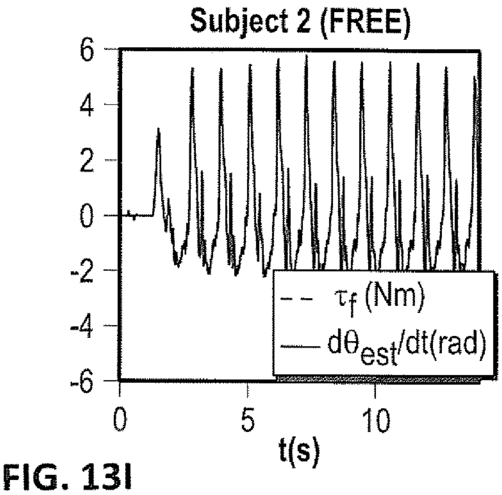
Figure 13J:
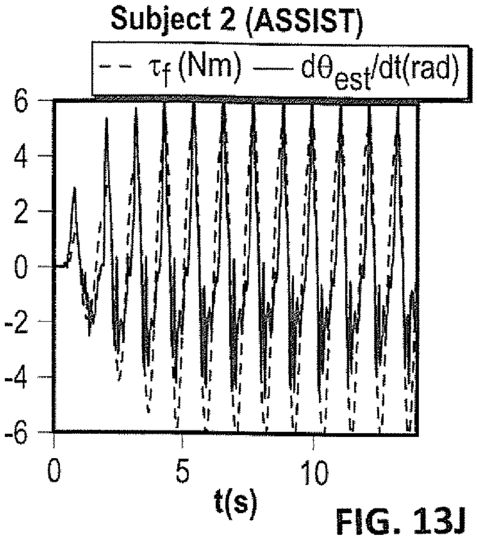
Figure 13K:
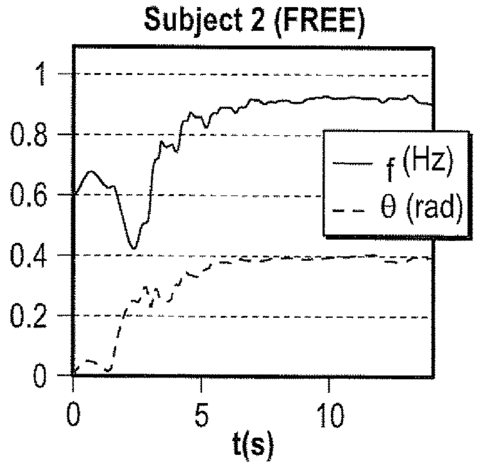
Figure 13L:
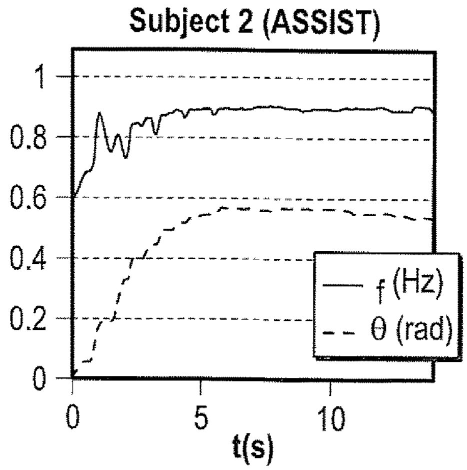

For example, one may assume that both stiffnesses may vary up to 50% of their respective nominal values. FIGS. 12A-12D shows the Nyquist plots for the analysis of the stability robustness of the human-exoskeleton system. FIGS. 12A-12B shows the Nyquist plots for $\delta k_h W_h(s)$, where $W_h(s)$ is the loop transfer function and the stiffness perturbation $\delta k_h$ acts as the feedback gain; each plot represents an extremal value of $\delta k_h$. FIGS. 12C-12D shows equivalent Nyquist plots for $\delta k_c W_c(s)$, where $W_c(s)$ is be the loop transfer function and $\delta k_c$ is the stiffness perturbation. The perturbed system remains stable in all cases.

FIGS. 12A-1.2B shows the Nyquist plots $\delta k_h \in [-0.5k_h, 0.5k_h]$ and FIGS. 12C-12D (b) $\delta k_h$ C $[-0.5k_c, 0.5k_c]$. It may be seen that the system remains stable as indicated by the plots' distance to the critical point −1. In the case of the joint stiffness, the lowest variation margin corresponds to the extreme negative value of $\delta k_h$. Thus, for the purposes of control design, it may be safer to underestimate the nominal value of joint stiffness $k_h$ so that the real value may involve a positive variation.

In the case of the coupling stiffness it may be observed that, for positive values of $\delta k_c$, the phase of the Nyquist plot never reaches 180° and therefore the variation margin is infinite, whereas for negative ok, there is a finite variation margin. Thus, in the case of the joint stiffness, for the purposes of design, it may be better to underestimate the stiffness of the coupling.

The above has presented a system and method for exoskeleton assistance based on producing a virtual modification of the dynamic properties of the lower limbs. The present control formulation may define assistance as an improvement in the performance characteristics of an LTI system representing the human leg, with the desired performance defined by a sensitivity transfer function modulating the natural admittance of the leg (equation (6)).

Figure 14:
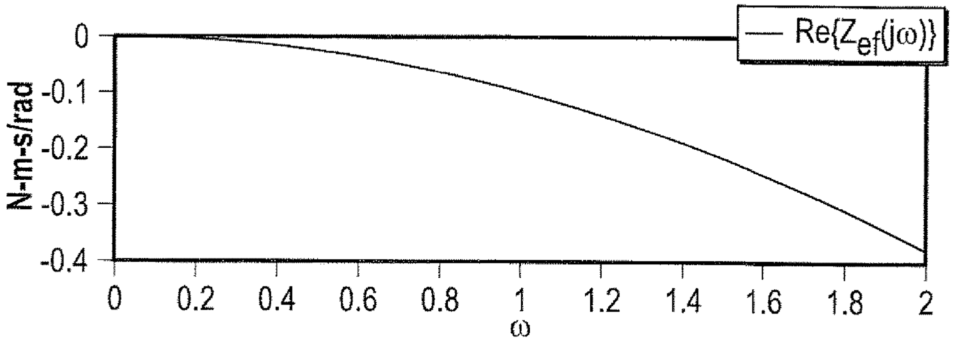
FIG. 14 is an illustrative graph showing exoskeleton port impedance: real part as a function of frequency in accordance with one aspect of the present application.

The relationship between positive feedback and assistance may be understood in terms of the work performed by the exoskeleton. FIG. 14 shows that the real part of the exoskeleton's impedance is negative for frequencies in the typical range of human motion. The physical interpretation of this behavior is that the exoskeleton's port impedance possesses negative damping, i.e. the exoskeleton acts as an energy source rather than a dissipator. This enables the exoskeleton to perform net positive work on the leg at every stride.

This behavior may exemplify an aspect of assistance, that for the exoskeleton to be useful, the exoskeleton may need to behave as an active system, i.e. act as an energy source. Thus, the present system and method departs from the well-known approach to the design of robotic systems that interact with humans; namely, that in order to guarantee stability the robot should display passive impedance at its interaction port (Colgate and Hogan, 1989). Although this may be useful from the point of view of safety, it may not be useful for exoskeletons, as a passive exoskeleton may be at best a device for temporary energy storage, not unlike a spring.

It may be worth noting that positive feedback may not be the only possible avenue for making an exoskeleton active. For example, in a more general version of the Bode sensitivity integral theorem (Frazzoli, E., Dahleh, M. 6.241J "Dynamic Sys teens and Control." (2011) (MIT OpenCourseWare). URL ocw.mit.edu/courses), the integral may also become positive if the exoskeleton transfer function is in a non-minimum phase, i.e. has zeros in the RHP.

Positive feedback alone may not produce the desired performance. With pure positive feedback of the angular acceleration, regions of simultaneous performance and stability may not exist; the system can at most cancel the exoskeleton's inertia before becoming unstable. The second-order filter in the feedback compensator $Z_f(s)$ (47) overcomes this problem by generating regions of approximately simultaneous performance and stability, i.e. regions where the dominant poles of the closed-loop system are be at their target locations and the system is stable. The purpose of the second-order filter may be understood in terms of the root locus: the compensator poles—$\sigma_f \pm j\omega_{d,f}$ shape the system's root locus in such a way that it may pass through the location of the target dominant poles ($p^d_h$ in FIGS. 10A and 10B). Thus, the second-order filter in this application may be seen more as a pole placement device rather than a device for blocking frequency content.

The feedback compensator fulfills its role despite the fact that the objectives of performance and stability may conflict with each other. The conflict is illustrated by FIG. 10A. If the inertia compensation gain $I_c$ is raised gradually, as one pair of poles moves towards the target locations, another pair of poles move towards the RHP. But with the proper design, the target location may be reached first.

One may attempt to derive general principles by which the admittance shaping control may simultaneously satisfy performance and stability. As a first step, the present robustness analysis aims to establish lower values of coupling or hip joint stiffness correspond to lower stability margins, which suggest that for control design, it may be safer to underestimate those parameters. Further, one may need to consider how the choice of a specific performance target affects the controller's ability to achieve almost simultaneous performance and stability.

What follows is the derivation of some of the mathematical formulas employed above to describe the control method. The control method is formulated in terms of Laplace-domain transfer function. The notation employed is explained below.

Transfer Functions:

Z_(s): mechanical impedance

Y_(s): mechanical admittance

X_(s): integral of the mechanical admittance (X_(s) Y(s)/s)

H_(s): torque-to-torque open-loop transfer function

S_(s): sensitivity transfer function

L_(s): loop transfer function for root-locus analysis

N_(s): numerator of a rational transfer function

D_(s): denominator of a rational transfer function

W_(s): loop transfer function for robustness analysis (sec. 4)

Subscripts are used to indicate which subsystems are present in a particular transfer function h: human leg e: exoskeleton mechanism, consisting of the actuator and arm c: compliant coupling between the human leg and the exoskeleton mechanism, molded as a spring and damper.

f: feedback compensator for the exoskeleton

The first step in the mathematical derivation is to compute the target values for the dynamic response parameters of the assisted leg: computation. From (14), $$\omega_{n,h}^{d}=R_{\omega}\omega_{nh} \tag{68}$$

One may define an intermediate target integral admittance $X_{h,DC}(s)$ that differs from $X_h(s)$ only in the trailing coefficient of the denominator:

$$X_{h,DC}(s)=\frac{1}{I_h s^2+2I_h\zeta_h\omega_{nh}s+I_h\omega_{nh,DC}^2} \tag{69}$$

One may choose $\omega_{n,h,DC}$ such that $X_{h,DC}$ (s) meets the DC gain specification $R_{DC}$:

$$\frac{X_{h,DC}(0)}{X_h(0)}=\frac{\omega_{nh}^2}{\omega_{nh,DC}^2}=R_{DC} \tag{70}$$

yielding $$\omega_{nh,DC}=\omega_{nh}\sqrt{R_{DC}^{-1}} \tag{71}$$

Because the target integral admittance $X^d_h(s)$ and the intermediate target $X_{h,DC}(S)$ have the same DC gains (although in general they have different natural frequencies and different damping ratios), one may write:

$$X_h^d(0)=X_{h,DC}(0) \text{ or } \frac{1}{I_h^d\omega_{nh}^{d2}}=\frac{1}{I_h\omega_{nh,DC}^2} \tag{72}$$

Substituting $\omega^d_{nh}$ with (68) and $\omega_{nh,DC}$ with (71) in (72) one obtains the value for $I^d_h$:

$$I_h^d=\frac{I_h}{R_{DC}R_\omega^2} \tag{73}$$

In order to obtain $\zeta^d_h$, one may compute the values of the resonant peaks for $X_h(j\omega)$ using equation (12) and $X^d_h(j\omega)$ using equation (13)

$$M_h=\frac{1}{2I_h\omega_{nh}^2\zeta_h\sqrt{1-\zeta_h^2}} \text{ for } X_h(j\omega) \tag{74}$$

and $$M_h^d=\frac{1}{2I_h^d\omega_{nh}^{d2}\zeta_h^d\sqrt{1-\zeta_h^{d2}}} \text{ for } X_h^d(j\omega) \tag{75}$$

Computing the ratio $M^d_h/M_h$ and applying (73) yields:

$$\frac{M_h^d}{M_h}=\frac{R_{DC}\zeta_h\sqrt{1-\zeta_h^2}}{\zeta_h^2\sqrt{1-\zeta_h^{d2}}} \tag{76}$$

Equating the right-hand side of (76) to $R_M$ (definition (15)) yields:

$$\zeta_h^2\sqrt{1-\zeta_h^{d2}}=\frac{R_{DC}}{R_M}\zeta_h\sqrt{1-\zeta_h^2} \tag{77}$$

Now one may define the right-hand side of (77) as:

$$\rho=\frac{R_{DC}}{R_M}\zeta_h\sqrt{1-\zeta_h^2} \tag{78}$$

yielding $$\zeta_h^{d4}-\zeta_h^{d2}+\rho^2=0 \tag{79}$$

for which the solution that ensures the existence of a resonant peak is:

$$\zeta_h^d=\sqrt{\frac{1-\sqrt{1-4\rho^2}}{2}} \tag{80}$$

Given a target dominant pole $p^d_h$, the phase of $L_{hecf}(p^d_h)$ is computed as:

$$\Phi(\sigma_f,\omega_{d,f},p_h^d)=\sum_{i=1}^{N_z}\psi_i-\sum_{i=1}^{N_p}\phi_i-\phi_f-\overline{\phi}_f \tag{81}$$

where $$\begin{aligned}\psi_i&=\arctan\left(\frac{\mathrm{Im}\{p_h^d-z_{hec,i}\}}{\mathrm{Re}\{p_h^d-z_{hec,i}\}}\right)\\ \phi_i&=\arctan\left(\frac{\mathrm{Im}\{p_h^d-p_{hec,i}\}}{\mathrm{Re}\{p_h^d-p_{hec,i}\}}\right)\\ \phi_f&=\arctan\left(\frac{\mathrm{Im}\{p_h^d\}-\omega_{d,f}}{\mathrm{Re}\{p_h^d\}+\sigma_f}\right)\\ \overline{\phi}_f&=\arctan\left(\frac{\mathrm{Im}\{p_h^d\}+\omega_{d,f}}{\mathrm{Re}\{p_h^d\}+\sigma_f}\right)\end{aligned} \tag{82}$$

Here $z_{hec,i}$ are the zeros of $L_{hecf}(s)$ and $p_{hec,i}$ are the poles of $L_{hecf}(s)$ excepting those at $s=-\sigma_f\pm j\omega_{d,f}$, so $N_p=N_2=4$. A valid solution for $\sigma_f$ and $\omega_{d,f}$ satisfies $\Phi(\sigma_f, \omega_{df}, p^d_h)=0$ for positive feedback.

Given a solution for $\sigma_f$ and $\omega_{d,j}$, the magnitude of the gain loop (see (51)) is computed as:

$$|K_L(\sigma_f,\omega_{d,f},p_h^d)|=\mathcal{K}_{L,f}\overline{\mathcal{K}}_{L,f}\mathcal{K}_{L,hec} \tag{83}$$

where $$\begin{aligned}\mathcal{K}_{L,f}&=\left[(\mathrm{Re}\{p_h^d\}+\sigma_f)^2+(\mathrm{Im}\{p_h^d\}-\omega_{d,f})^2\right]^{\frac{1}{2}}\\ \overline{\mathcal{K}}_{L,f}&=\left[(\mathrm{Re}\{p_h^d\}+\sigma_f)^2+(\mathrm{Im}\{p_h^d\}+\omega_{d,f})^2\right]^{\frac{1}{2}}\\ \mathcal{K}_{L,hec}&=\frac{\prod_{i=1}^{N_p}\left[\mathrm{Re}\{p_h^d-p_{hec,i}\}^2+\mathrm{Im}\{p_h^d-p_{hec,i}\}^2\right]^{\frac{1}{2}}}{\prod_{i=1}^{N_z}\left[\mathrm{Re}\{p_h^d-z_{hec,i}\}^2+\mathrm{Im}\{p_h^d-z_{hec,i}\}^2\right]^{\frac{1}{2}}}\end{aligned} \tag{84}$$

The present system and method may be used for lower-limb exoskeleton control that assists by producing desired dynamic response for the human leg. When wearing the exoskeleton device, the system and method may be seen as replacing the leg's natural admittance with the admittance of the coupled system (i.e., the leg and exoskeleton system). The system and method use a controller to make the leg obey an admittance model defined by target values of natural frequency, peak magnitude and zero-frequency response. The system and method does not require any estimation of muscle torques or motion intent. The system and method scales up the coupled system's sensitivity transfer function by means of a compensator employing positive feedback. This approach increases the leg's mobility and makes the exoskeleton an active device capable of performing net work on the limb. While positive feedback is usually considered destabilizing, the system and method provides performance and robust stability through a constrained optimization that maximizes the system's gain margins while ensuring the desired location of its dominant poles The foregoing description is provided to enable any person skilled in the relevant art to practice the various embodiments described herein. Various modifications to these embodiments will be readily apparent to those skilled in the relevant art, and generic principles defined herein may be applied to other embodiments. All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public.

What is claimed is:

1. An exoskeleton system for assisted movement of legs of a user comprising:

a harness worn around a waist of the user;

a pair of arm members coupled to the harness and to the legs;

a pair of motor devices, wherein one of the pair of motor devices is coupled to a corresponding arm member of the pair of arm members moving the pair of arm members for assisted movement of the legs; and a controller coupled to the motor controlling movement of the assisted legs, the controller shaping an admittance of the system facilitating movement of the assisted legs by generating a target DC gain, a target natural frequency and a target resonant peak, wherein the controller comprises:

an angle feedback compensator; and an angular acceleration feedback compensator.

2. The exoskeleton system of claim 1, wherein the angle feedback compensator generates a target DC gain.

3. The exoskeleton system of claim 1, wherein the angle feedback compensator generates a target DC gain on the leg's admittance to compensate for the stiffness and gravitational torque on the legs.

4. The exoskeleton system of claim 1, wherein the angular acceleration feedback compensator generates a target natural frequency and target resonant peak.

5. The exoskeleton system of claim 4, wherein the angular acceleration feedback compensator generates target values of natural frequency and resonant peak magnitude of the leg's admittance.

6. The exoskeleton system of claim 1, wherein the dynamics of the leg are modeled as the transfer function of a linear time-invariant (LTI) system, the controller replacing the natural admittance of the leg by the equivalent admittance of the coupled system formed by the leg and the exoskeleton.

7. The exoskeleton system of claim 1, wherein the desired dynamic response of the assisted leg is given by an integral admittance model defined by $X^d_h(s)=I/I^d_h(s^2+2\zeta^d_h\omega^d_{nh}s+\omega^d_{nh}{}^2)$, where $I^d_h$, $\omega^d_{nh}$, and $\zeta^d_h$ are desired values of the inertia moment, natural frequency and damping ratio of the leg.

8. The exoskeleton system of claim 4, wherein the angular acceleration feedback compensator matches the dominant poles of the coupled system with those of the target admittance, through a pole placement technique.

9. The exoskeleton system of claim 3, wherein the angular acceleration feedback compensator prevents dominant poles from crossing to a right-hand side of a complex plane (RHP) or imaginary poles.

10. A device for controlling an exoskeleton system comprising:

a controller shaping an admittance of the system facilitating movement of assisted legs coupled to the system, wherein the controller models dynamics of one of the legs as a transfer function of a linear time-invariant (LTI) system, the controller replacing admittance of the one of the legs by an approximate equivalent admittance of a coupled leg and system by generating a target DC gain, a target natural frequency and a target resonant peak.

11. The device of claim 10, wherein the controller approximately matches a dynamic response of the assisted legs to an integral admittance model defined as $X^d_h(s)=I/I^d_h(s^2+2\zeta^d_h\omega^d_{nh}s+\omega^d_{nh}{}^2)$, where $I^d_h$, $\omega^d_{nh}$, and $\zeta^d_h$ are predefined values of the inertia moment, natural frequency and damping ratio of the one of the legs.

12. The device of claim 10, wherein the controller comprises: an angle feedback compensator; and an angular acceleration feedback compensator.

13. The device of claim 12, wherein the angle feedback compensator generates the target DC gain.

14. The device of claim 12, wherein the angle feedback compensator generates the target DC gain compensating for stiffness and gravitational torque on the legs.

15. The device of claim 12, wherein the angular acceleration feedback compensator generates the target natural frequency and target resonant peak.

16. The device of claim 12, wherein the angular acceleration feedback compensator increases a natural frequency of the legs and a magnitude peak of the legs admittance.

17. The device of claim 14, wherein the angular acceleration feedback compensator matches dominant poles with the target admittance through a pole placement technique.

18. A method for an exoskeleton assistive control comprising:

calculating ratios between unassisted leg movement and a desired value through natural frequencies, resonant peaks and DC gains of the exoskeleton;

calculating angular position feedback gain $k_{DC}$ of the exoskeleton system;

calculating target admittance parameters $\omega^d_{nh}$ and $\zeta^d_h$;

obtaining a dominant pole of a target admittance as $p_h{}^d=-\sigma_h{}^d+jw_{dh}{}^d$;

obtaining parameters $\{\sigma_f, \omega_{d,f}\}$ of a feedback compensator of the exoskeleton system; and obtaining a loop gain $K_L$ and an inertia compensation gain $I_c$ of the coupled exoskeleton system and legs of a user.

19. The method of claim 18, wherein obtaining the parameters $\{\sigma_f, \omega_{d,f}\}$ of the feedback compensator of the exoskeleton system comprises performing constrained optimization.

* * * * *